US010905658B2

(12) United States Patent
Bhagwat

(10) Patent No.: US 10,905,658 B2
(45) Date of Patent: Feb. 2, 2021

(54) METHODS AND COMPOSITIONS FOR DETECTING HEMATOPOIETIC AND LYMPHOID TISSUE CANCER CELLS

(71) Applicant: WAYNE STATE UNIVERSITY, Detroit, MI (US)

(72) Inventor: Ashok S. Bhagwat, Livonia, MI (US)

(*) Notice: Subject to any disclaimer, the term of this patent is extended or adjusted under 35 U.S.C. 154(b) by 0 days.

(21) Appl. No.: 16/067,986

(22) PCT Filed: Jan. 5, 2017

(86) PCT No.: PCT/US2017/012279
§ 371 (c)(1),
(2) Date: Jul. 3, 2018

(87) PCT Pub. No.: WO2017/120296
PCT Pub. Date: Jul. 13, 2017

(65) Prior Publication Data
US 2019/0022032 A1 Jan. 24, 2019

Related U.S. Application Data

(60) Provisional application No. 62/274,939, filed on Jan. 5, 2016.

(51) Int. Cl.
A61K 31/137 (2006.01)
A61K 31/4188 (2006.01)
A61K 31/13 (2006.01)
A61K 31/17 (2006.01)
C12Q 1/6886 (2018.01)
G01N 33/574 (2006.01)
A61P 35/00 (2006.01)

(52) U.S. Cl.
CPC ............ A61K 31/137 (2013.01); A61K 31/13 (2013.01); A61K 31/17 (2013.01); A61K 31/4188 (2013.01); A61P 35/00 (2018.01); C12Q 1/6886 (2013.01); G01N 33/574 (2013.01)

(58) Field of Classification Search
CPC ...... A61K 31/13; A61K 31/137; A61K 31/17; A61K 31/4188; C12Q 1/6886; G01N 33/574; C01B 21/08; A61P 35/00
See application file for complete search history.

(56) References Cited

U.S. PATENT DOCUMENTS 5,346,911 A * 9/1994 Augelli-Szafran .......... C07D 211/72 514/339
2010/0267657 A1 10/2010 Liu et al.

OTHER PUBLICATIONS

El-Sagheer et. al., Chemical Society Reviews, 2010, The Royal Soc of Chem, vol. 39, pp. 1388-1405 (Year: 2010).*
Sane et. al., Journal of Polymer Science, 2013, Wiley Periodicals Inc., vol. 51, pp. 2091-2103 (Year: 2013).*
Suchanova et. al., Bioconjugate Chemistry, 2016, ACS, vol. 28, pp. 307-313 (Year: 2016).*
O-Prop-2-ynyl-hydroxylamine, Compound Summary, PubChem, pubchem.ncbi.nlm.nih.gov/compound/10749134, retrieved May 16, 2019, 12 pages.
Shalout et al., Genomic Uracil Homeostasis during Normal B Cell Maturation an dLoss of This Balance during B Cell Cancer Development. Molecular and Cellullar Biology 2014;34(21)4019-32.
Wei et al., A novel class of chemicals that reatct with abasic sites in DNA and specifically kill B cell cancers. PLoS One. Sep. 2017;12(9):e0185010.
Wei et al., A versatile new tool to quantify abasic sites in DNA and inhibit baseexcision repair. DNA Repair. Jan. 2015;27:9-18.
Wei, Development of a Novel Class of Chemicals for Labeling Abasic Sites in Cellular DNA and Killing Cancer Cells. Dissertation, Wayne State University, 2016, 1669, 137 pages.
Wei et al., A novel class of chemicals that reatct with damaged DNA and specifically kill B-cell cancers. Abstract 3757, Proceedings: AACR 107th Annual Meeting, Apr. 16-20, 2016, New Orleans, LA, 4 pages.
Extended European Search Report for EP 17736301, dated Jul. 31, 2019, 9 pates.

* cited by examiner

Primary Examiner — Sarah Pihonak
(74) Attorney, Agent, or Firm — Casimir Jones, S.C.; Mary Ann D. Brow

(57) ABSTRACT

A method for killing hematopoietic and/or lymphoid tissue cancer cells is provided. The method includes a step identifying a subject having hematopoietic and/or lymphoid tissue cancer with circulating cells or DNA containing elevated levels of uracils and AP sites. The hematopoietic and/or lymphoid tissue cancer cells are contacted (i.e., treated) with an alkoxyamino compound having formula I:

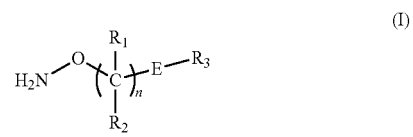

wherein:
E is

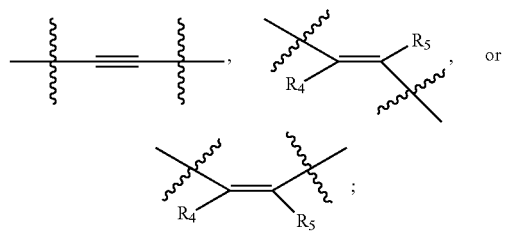

$R_1$, $R_2$, $R_3$, $R_4$, $R_5$ are each independently hydrogen (H), $C_{1-6}$ alkyl, F, Cl, or Br; and n is 1 to 5.

9 Claims, 35 Drawing Sheets

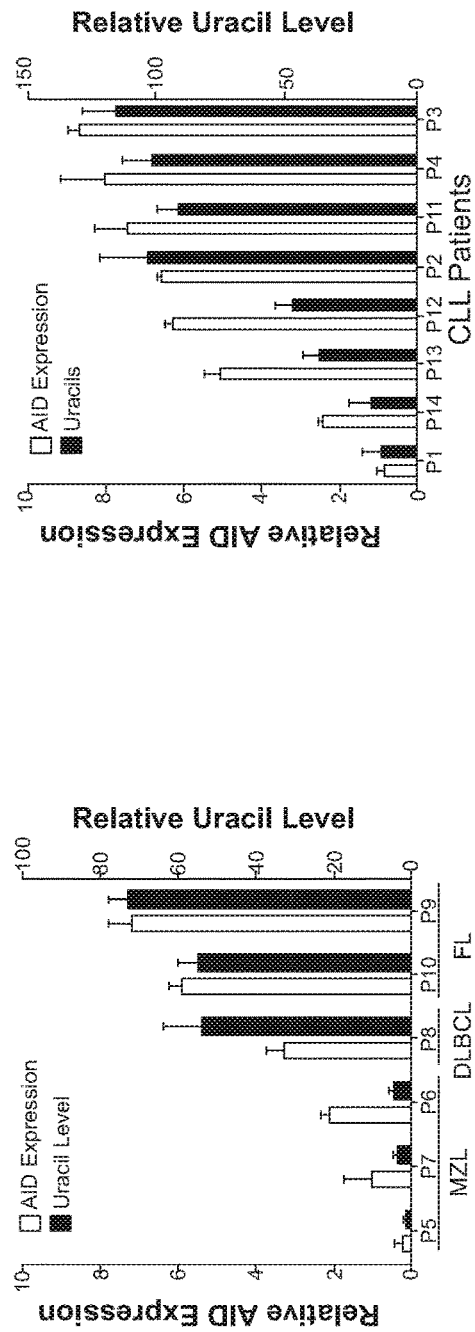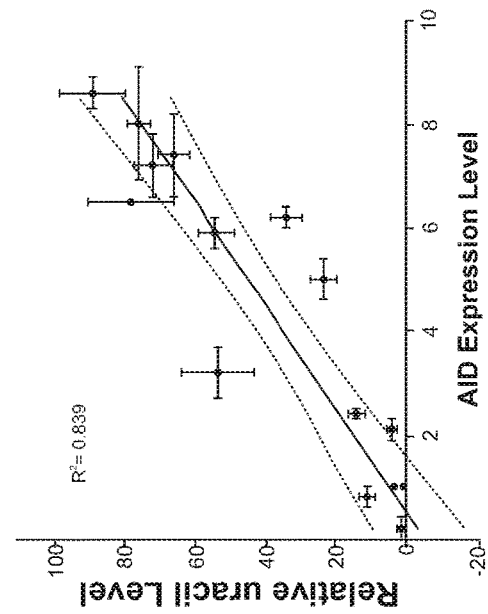
FIG. 2A   FIG. 2B   FIG. 2C

Methoxyamine
(O-methylhydroxlamin

AA3
(O-(prop-2-yn-1-yl)hydroxylamine)

AA7
(O-(prop-2-en-1-yl)hydroxylamine)

Aldehyde-reactive probe (ARP)
N-(3-(aminooxy)propanoyl)-5-((3aS,4S,6aR)-2-oxohexahydro-
H-thieno[3,4-d]imidazol-4-yl)pentanehydrazide

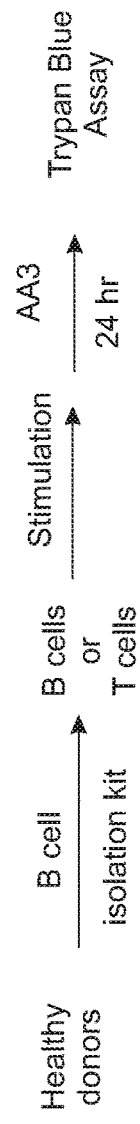
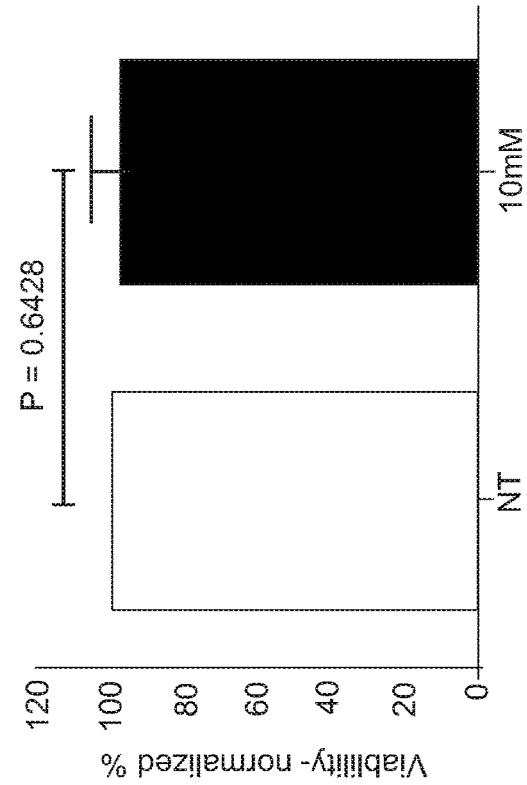
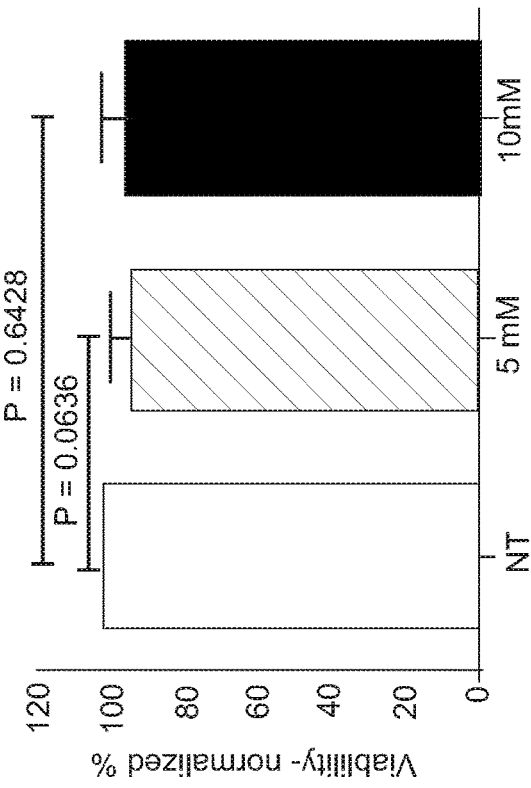
FIG. 15A
FIG. 15B
FIG. 15C

Scheme 1. Synthesis of AA3

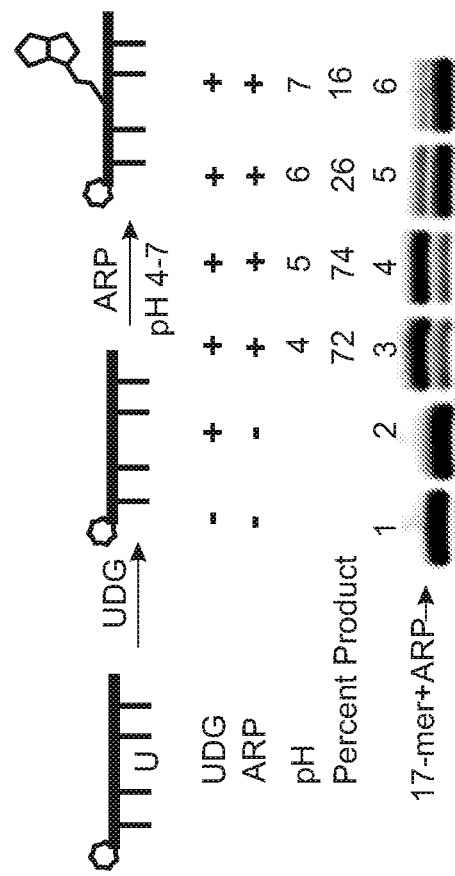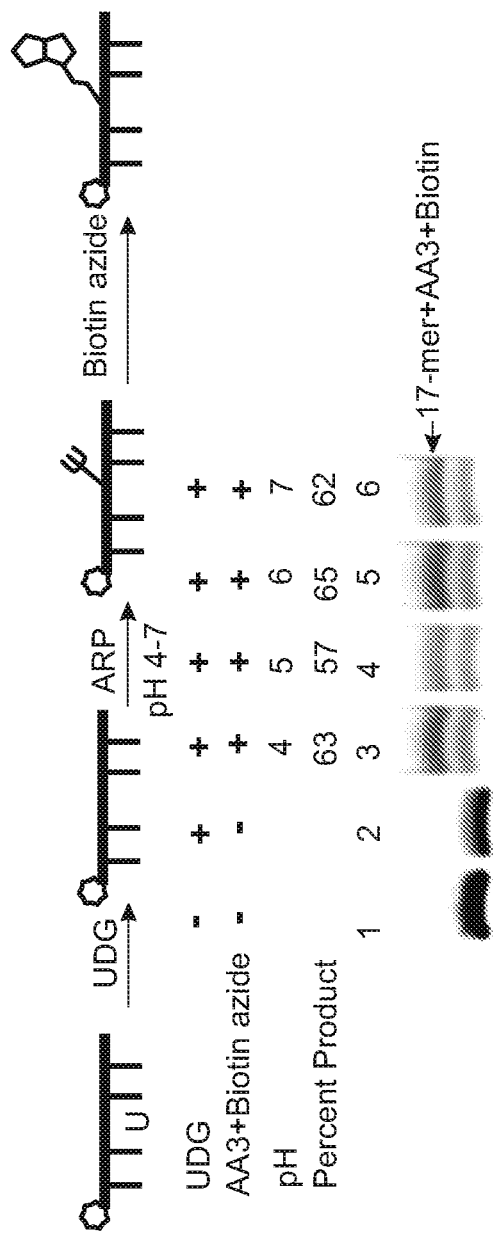
FIG. 23A
FIG. 23B

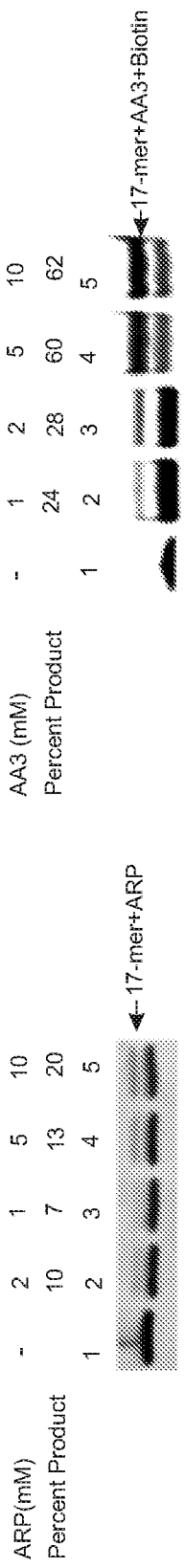
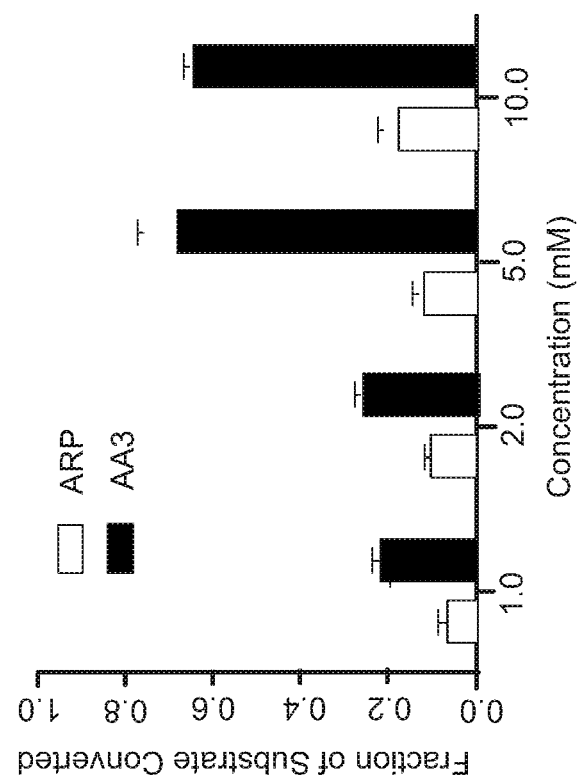
FIG. 24A
FIG. 24B
FIG. 24C

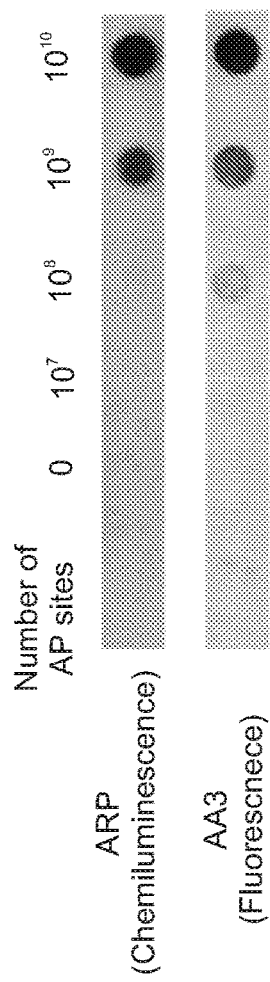
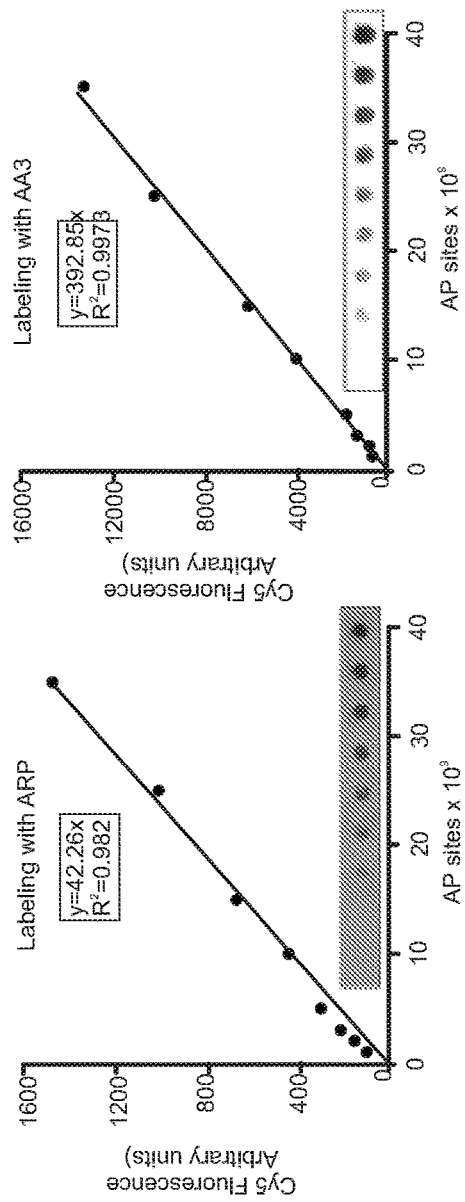
Fig. 26A
Fig. 26B

METHODS AND COMPOSITIONS FOR DETECTING HEMATOPOIETIC AND LYMPHOID TISSUE CANCER CELLS

CROSS-REFERENCE TO RELATED APPLICATIONS

This application is the U.S. national phase of PCT Appln. No. PCT/US2017/012279 filed Jan. 5, 2017 which claims the benefit of U.S. provisional application Ser. No. 62/274,939 filed Jan. 5, 2016, the disclosures of which are incorporated in their entirety by reference herein.

STATEMENT REGARDING FEDERALLY SPONSORED RESEARCH OR DEVELOPMENT

The invention was made with Government support under Contract No. R01 GM057200 awarded by the National Institutes of Health. The Government has certain rights to the invention.

TECHNICAL FIELD

In at least one aspect, the present invention is related to methods for selectively killing hematopoietic and/or lymphoid tissue cancer cells.

BACKGROUND

Hematologic cancers constitute about 10% of all cancers. In the U.S. over 70,000 new cases of non-Hodgkin lymphomas are found per year and 80% of these are B cell cancers (B-NHL). Annually, about 20,000 deaths occur due to this disease. Additionally, there are other types of B cell malignancies including leukemias and myelomas.

Approximately half of the B cell cancers originate during the development of these cells in germinal centers. During normal germinal center development and enzyme called activation-induced deaminase (AID) is expressed in B cells. This enzyme converts cytosines in DNA to uracil, which is an abnormal base. This results in the creation of beneficial mutations in the antibody gene—a process called somatic hypermutation. However, in some cells this process becomes unregulated causing cancer. In these cells, the genome contains a high level of uracils and when the cell tries to repair these uracils it creates apurinic/apyrimidinic sites (AP sites). Some AP sites may be repaired or "tolerated", while others cause cell death.

Currently, drugs that kill cancer cells by reacting with abasic sites in DNA are not known. The only chemical that reacts with abasic sites and is being tested in anti-cancer therapy is methoxyamine (MX). MX has been proposed as an anticancer chemotherapy agent in combination with a monoalkylating agent such as Temozolomide. The alkylating agent creates DNA base damage that is excised by a DNA glycosylase creating AP sites, and reaction of MX with AP sites blocks further repair killing the cell. Multiple NCI-approved clinical trials using MX as one part of combination chemotherapy are underway.

Accordingly, there is a need for improved methods for treating hematopoietic and/or lymphoid tissue cancers.

SUMMARY

The present invention solves one or more problems of the prior art by providing a method for killing hematopoietic and/or lymphoid tissue cancer cells. The method includes a step of identifying a subject having hematopoietic and/or lymphoid tissue cancer cells. The hematopoietic and/or lymphoid tissue cancer cells are contacted with an alkoxyamine compound having formula I:

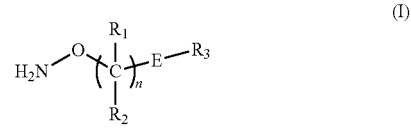

wherein:
E is

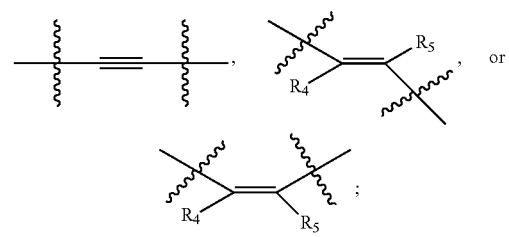

$R_1$, $R_2$, $R_3$, $R_4$, $R_5$ are each independently hydrogen (H), $C_{1-6}$ alkyl, F, Cl, or Br; and n is 1 to 5.

The present invention shows that that alkoxyamines with terminal alkyne functionality (C≡C bond) are selectively toxic for B cell cancers that express AID without the need for other DNA damaging agents such as Temozolomide. The prototype of these compounds, AA3, reacts with abasic sites in DNA and kills a number of human B cell cancer cell lines, but none of the non-hematological cancer lines. It also does not kill normal human B or T cells or murine B cells. AA3 reacts with the excess abasic sites present in the B cell cancer genomes and accumulates as a covalent adduct of its DNA. This leads to the creation of a large number of double-strand breaks and this is the likely cause of cell death. The terminal C≡C bond in AA3 is required for its cytotoxicity providing a prototype framework upon which new and better anticancer compounds can be synthesized.

BRIEF DESCRIPTION OF THE DRAWINGS

FIGS. 2A, 2B, and 2C. Quantification of AID gene expression and genomic uracils in B-NHL tumor cells. A—Lymphoma patients; B—Chronic lymphocytic leukemia (CLL) patients; C—Statistical correlation between AID expression and genomic uracils in B-NHL cancer patient tumors.

FIG. 15A is a flow chart showing the isolation and treatment of B or T cells with AA3.

FIG. 15B is a bar chart showing that AA3 does not kill normal B cells.

FIG. 15C is a bar chart showing that AA3 does not kill normal T cells.

FIGS. 23A and 23B. pH dependence of reaction of ARP and AA3 with AP-sites. A scheme for each experiment is shown at the top of each part of the figure. (A) Reactions of ARP (5 mM) with AP sites at pH 4, 5, 6 and 7 (lanes 3 through 6). (B) Reactions of AA3 (5 mM) with AP sites at pH 4, 5, 6 and 7 (lanes 3 through 6) followed by the addition of biotin azide.

FIGS. 24A, 24B, and 24C. Concentration dependence of reactivity of ARP and AA3 with AP sites at pH 7. (A) DNA was incubated with UDG to create AP sites and reacted with 2, 1, 5, or 10 mM ARP (lanes 2 through 5). (B) DNA was incubated with UDG to create AP sites and reacted with 1, 2, 5, or 10 mM AA3 (lanes 2 through 5) followed by click reaction with biotin azide. (C) Quantification of the reaction products of different concentrations of ARP and AA3 with AP sites at pH 7. Mean and standard deviation of triplicate samples are shown.

FIGS. 26A and 26B. Sensitivity of detection of AP sites using ARP and AA3. (A) Image of the nylon membranes where different amounts of DNA containing a synthetic oligomer with one AP site were labeled using either ARP-HRP (top) or AA3-Cy5 (bottom). (B) Synthetic duplex containing one AP site was labeled with either ARP or AA3. Different dilutions of ARP-labeled DNA was spotted on a membrane and bound with Cy5-streptavidin. AA3-labeled DNA was reacted with Cy5 azide and different dilutions were spotted on a membrane. Cy5 fluorescence was quantified in each case and is plotted against the number of AP sites in each spot. (Inset) Image of the membrane in each case.

DETAILED DESCRIPTION

Figure 1A:
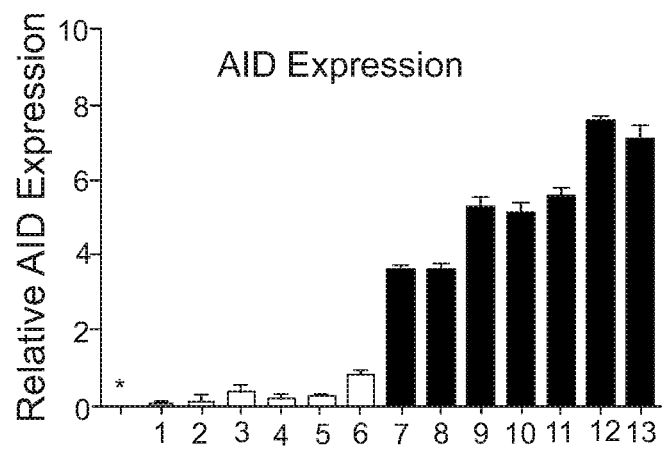
FIGS. 1A and 1B. Quantification of AID gene expression (A) and genomic uracils (B) in normal human cells and cancer cell lines. T-cell: T cell lymphoma; cHL: classical Hodgkin lymphoma; MM: multiple myeloma; FL: Follicular lymphoma; DLBCL: Diffuse large B cell lymphoma; Burkitt: Burkitt lymphoma.

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; "R" groups include H, $C_{1-10}$ alkyl, $C_{2-10}$ alkenyl, $C_{6-14}$ aryl (e.g., phenyl, halo, or $C_{4-14}$ heteroaryl); single letters (e.g., "n" or "o") are 1, 2, 3, 4, or 5; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, that a wavy line crossing a straight solid line indicates the point of attachment for a functional group.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Abbreviations

"AA3" refers to O-(prop-2-yn-1-yl)hydroxylamine.
"AA4" refers to O-(n-propyl)hydroxylamine.
"AA5" refers to O-(but-3-yn-1-yl)hydroxylamine.
"AA6" refers to 0-(2-azidoethyl)hydroxylamine
"AA7" refers to O-allylhydroxylamine
"AID" refers to activation-induced deaminase.
"ARP" refers to aldehyde-reactive probe.
"DLBCL" refers to diffuse large B cell lymphoma.
"MX" refers to methoxyamine.

The term "subject" refers to a human or animal, including all mammals such as primates (particularly higher primates), sheep, dog, rodents (e.g., mouse or rat), guinea pig, goat, pig, cat, rabbit, and cow.

The term "fluorophore" as used herein means a fluorescent chemical moiety that can re-emit light upon light excitation. Examples of fluorophores, include, but are not limited to, dansyl, fluorescein and its derivatives, cyanine dyes (for example, Cy3, Cy5, etc.), TAMRA and its derivatives, rhodamines and its derivatives, Alexa Fluor analogs, IR dyes, ATTO dyes, Texas Red, Oregon Green, coumarin, acridine dyes, BODIPY, and Qdot probes.

Figure 1B:
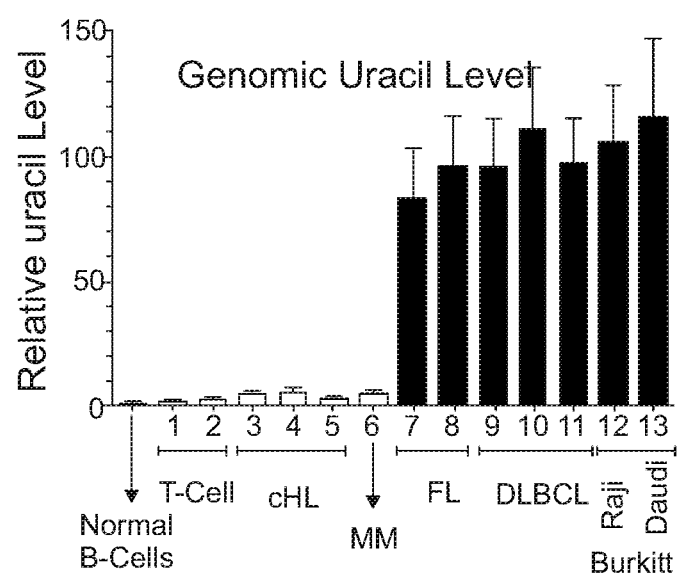
Figure 3:
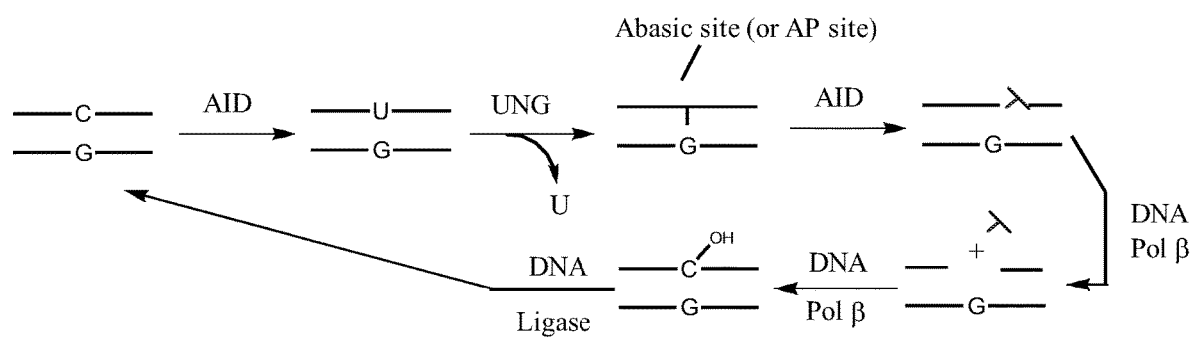
FIG. 3 is a schematic showing that repair of AP sites occurs through a Base-excision Repair Pathway; uracils created by an enzyme called AID are excised by the DNA glycosylase UNG. The resulting AP sites are cleaved by APE-1 endonuclease and further repaired through the action of DNA polymerase β and DNA ligase I or III.
Figure 4:
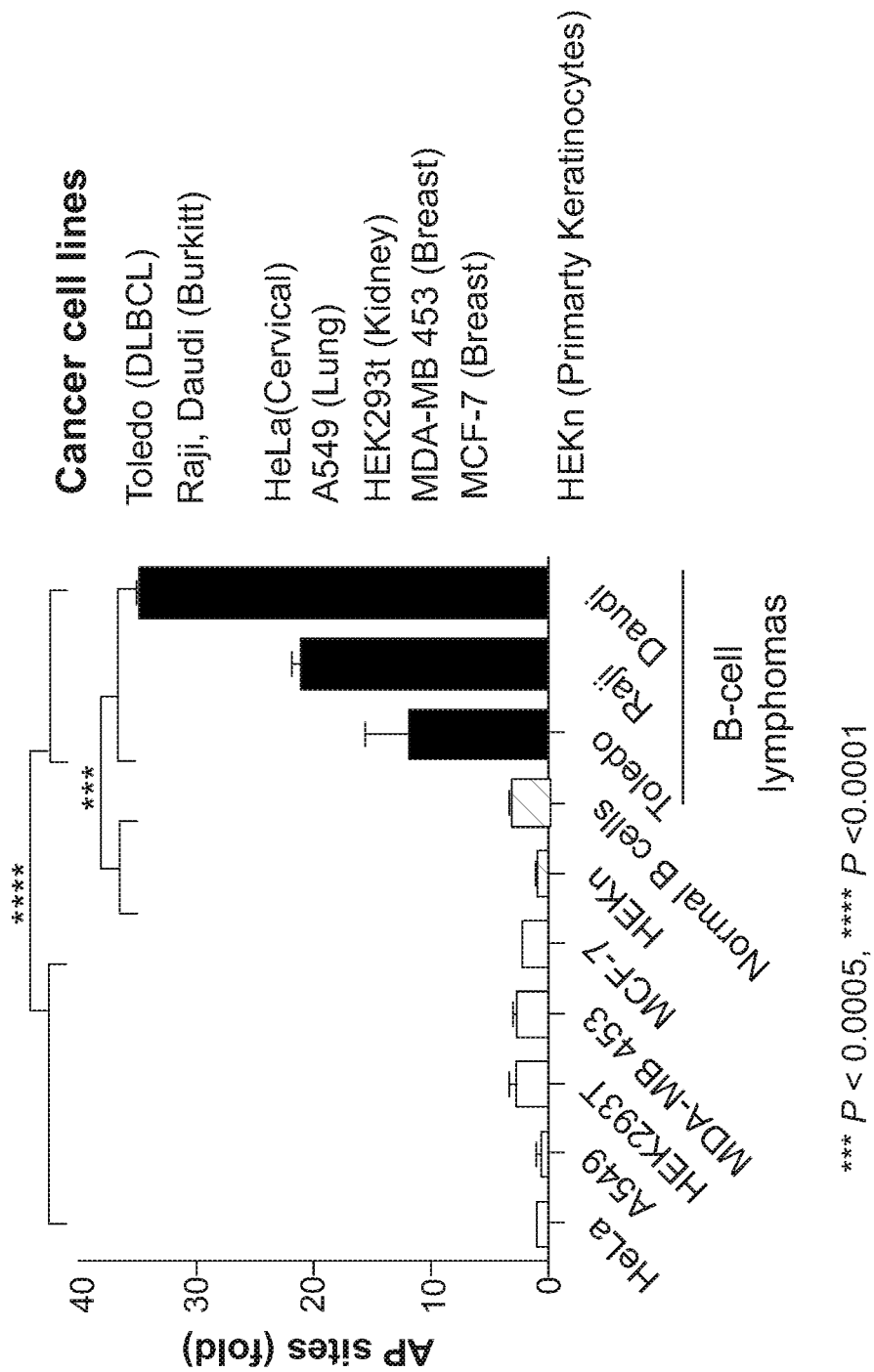
FIG. 4. B cell lymphoma cells accumulate AP sites in their genomes. "*" is P-value<0.001; "**" is P-value<0.0001.
Figure 5:
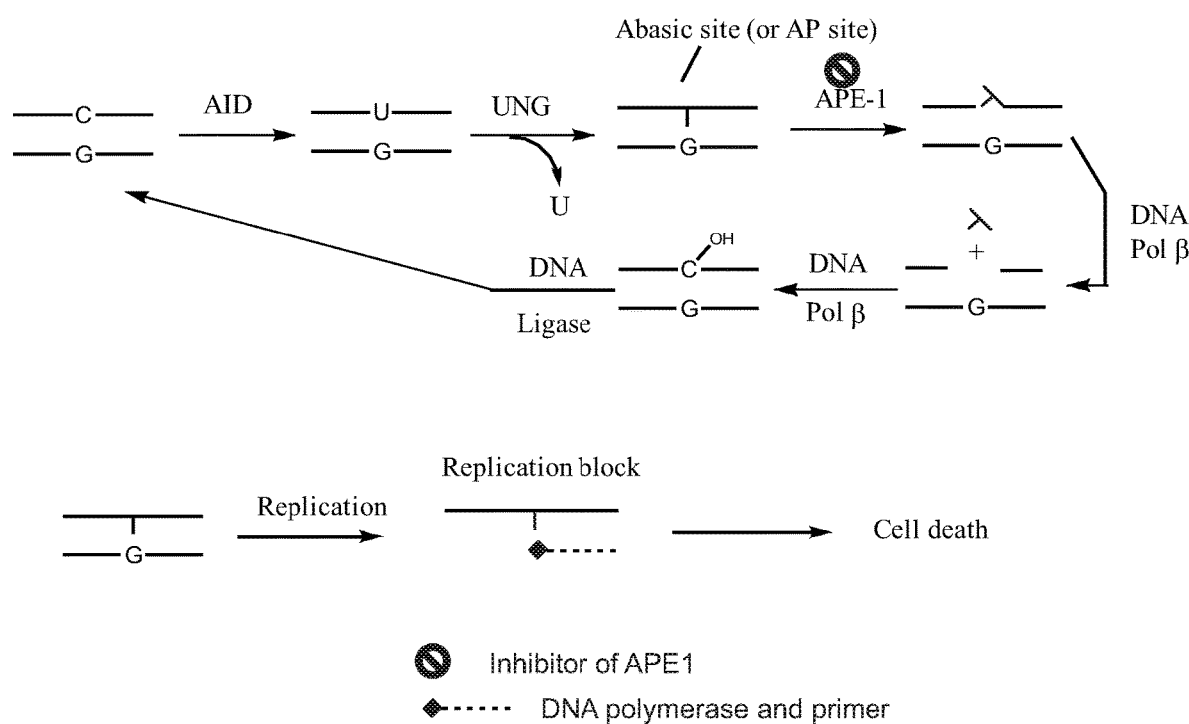
FIG. 5 is a schematic showing that inhibition of repair of AP sites may selectively kill B cell cancers.
Figure 6A:
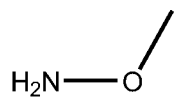
FIGS. 6A and 6B show the structure of alkoxyamines (A) and reaction of AA3 with abasic sites (B).
Figure 6A:
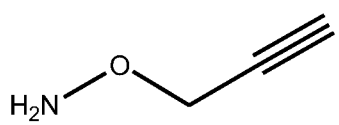
Figure 6A:
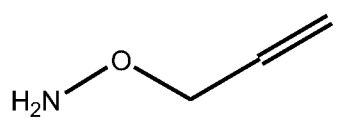
Figure 6A:
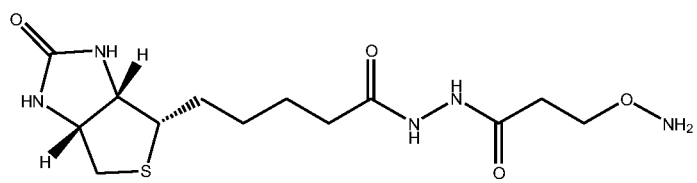
Figure 6B:
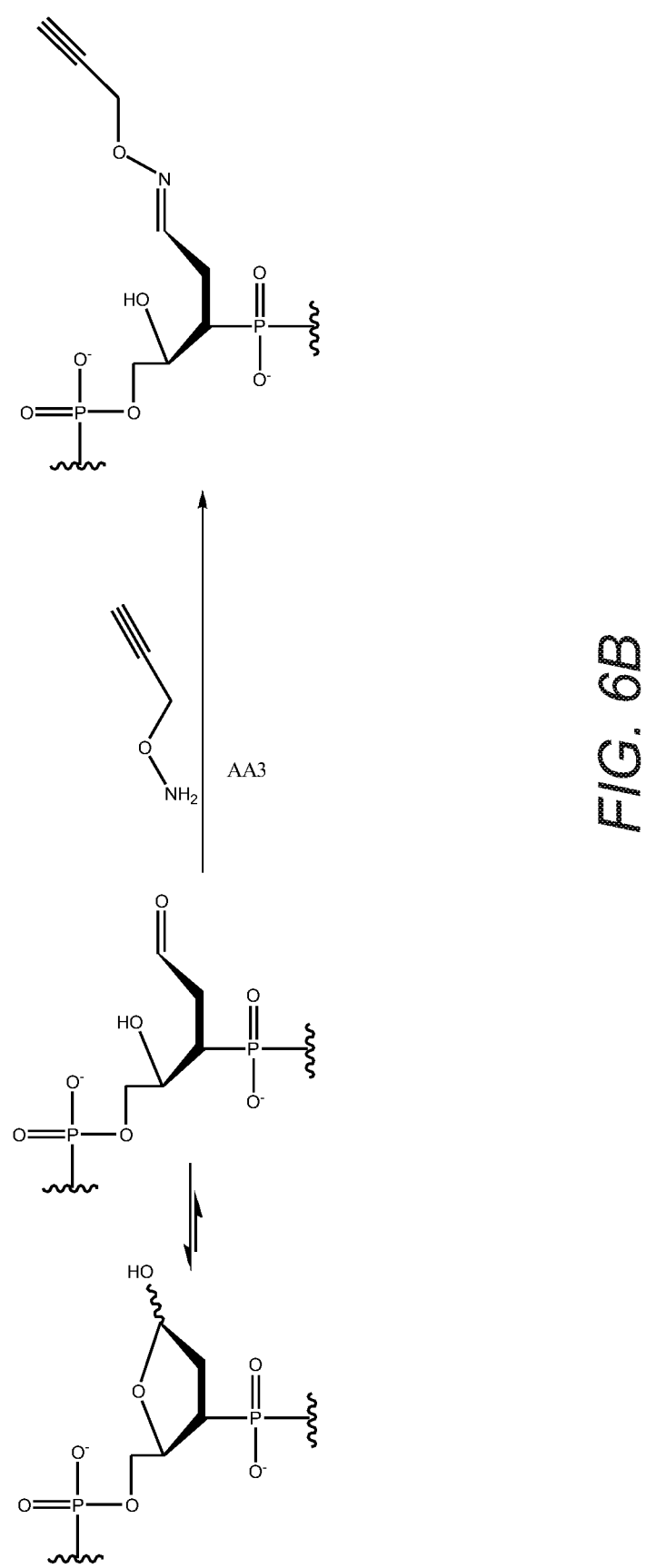

In various embodiments of the present invention, a class of chemicals that selectively react with DNA of B-NHL cells leading to their death is provided. This class of chemicals can also be used to monitor progression or relapse of the disease in the patients. These chemicals are based on our recent finding that most B-NHL cells contain an excess of a specific type of damage in their DNA called abasic sites (a.k.a. apurinic/apyrimidinic sites or AP sites). AP sites are created in DNA when the cell tries to repair damage to DNA bases. Some AP sites may be repaired or "tolerated", while others cause cell death. Embodiments of the present invention provide alkoxyamine compounds that react with AP sites preventing their repair and hence leading to cell death. FIG. 1 shows that high levels of uracils are present in B-NHL cell lines and patient tumors. The slide shows that high levels of AID expression in hematological cancer cell lines is correlated with high levels of genomic uracils. Similarly, FIG. 2 shows that high levels of AID expression in different types of B-NHL patient tumor cells is correlated with high levels of genomic uracils. FIG. 3 shows the biochemical pathway for the repair of uracils in DNA. Specifically, it shows that cytosines in C:G pairs are converted to uracils by AID and the uracils are excised by the enzyme uracil-DNA glycosylase (UNG) creating AP sites. The AP sites are cleaved by an AP endonuclease (APE-1) and the subsequent action of DNA polymerase β and DNA ligase I or III results in the restoration of C:G pair avoiding mutations. This pathway suggests that when cells express high levels of AID and also contain UNG, their genomes should contain high levels of AP sites. FIG. 4 confirms this prediction by quantifying AP sites in three B-NHL cell lines and comparing the results with those from normal B cells, normal keratinocytes and non-hematological cancer cell lines. FIG. 4 shows that B-NHL cells contain about 5- to 15-fold higher levels AP sites than other human cells. The cancer-killing alkoxyamine compounds set forth below are based on these observations. Advantageously, the present invention seeks to prevent repair of AP sites in B-NHL genomes by inhibiting the enzyme APE-1 (FIG. 5). Inhibition of APE-1 should result in the accumulation of unrepaired AP sites in cells which are known to block DNA replication. Prevention of replication should result in cell death (FIG. 5).

Embodiments of the invention specifically kill B cell cancers that express an enzyme called activation-induced deaminase (AID) at high level. As set forth above B cell cancer cells that express AID at high levels contain high levels of a rare base, uracil, in their genome which cells try to remove by creating an excess of abasic sites. An alkoxyamine called AA3 (FIG. 6; O-(prop-2-yn-1-yl)hydroxylamine was designed to covalently tag abasic sites in DNA (FIG. 6). It was discovered that alkoxyamines like AA3 should kill B cell cancers because the genomes of these cancers contain high levels of abasic sites. Compelling evidence that AA3 links to excess abasic sites in the DNA in B cell cancers and kills them is presented below. AA3 has never been described as a direct killer of cancer cells and the mechanism of cell killing by AA3 has never been proposed for any anti-cancer drug. The structures of AA3 and two commercially available alkoxyamines that react with abasic sites, methoxyamine (O-methylhydroxylamine) and ARP (aldehyde-reactive probe; N'-(3-(aminooxy)propanoyl)-5-((3aS,4S,6aR)-2-oxohexahydro-H-thieno[3,4-d]imidazol-4-yl)pentanehydrazide), are presented in FIG. 6.

In one embodiment, a method for killing hematopoietic and/or lymphoid tissue cancer cells is provided. The method includes a step of identifying a subject having hematopoietic and/or lymphoid tissue cancer cells. The hematopoietic and/or lymphoid tissue cancer cells are then contacted with (i.e., treated with) an alkoxyamine compound having formula I:

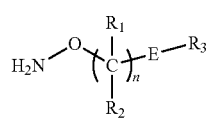

(I)

wherein:
E is

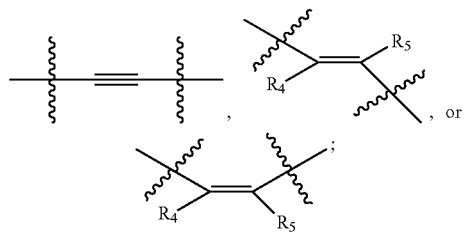

$R_1$, $R_2$, $R_3$, $R_4$, $R_5$ are each independently hydrogen (H), $C_{1-6}$ alkyl, F, Cl, or Br; and n is 1 to 5 (i.e., 1, 2, 3, 4, or 5, or a combination thereof).

Therefore, in one refinement, the alkoxyamine compound having formula I is described by formula II:

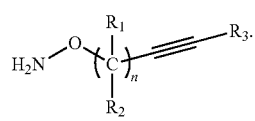

II

In another refinement, the alkoxyamine compound having formula I is described by formulae IIIA or IIIB:

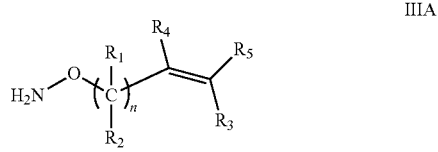

IIIA

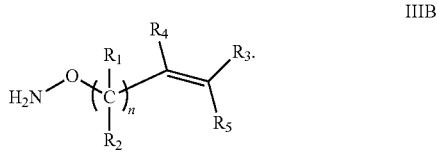

IIIB

In a variation, the subject having hematopoietic and/or lymphoid tissue cancer cells has been diagnosed with or is suspected of having hematopoietic and/or lymphoid tissue cancer. Therefore, this variation provides a method for treating hematopoietic and/or lymphoid tissue cancer is provided. The method includes a step of identifying a subject having hematopoietic and/or lymphoid tissue cancer. An alkoxyamine compound having formula I is administered to the subject. In this regard, it should also be appreciated that the variations described by formulae II, IIIA and IIB are also useful in this embodiment.

In refinements of the methods set forth above, the alkoxyamine compound having formula I is administered in such an amount that the subject achieves a blood concentration of the alkoxyamine compound having formula I of 100 µM to 20 mM. In another variation of the embodiments set forth above, the alkoxyamine compound having formula I is administered in such an amount that the subject achieves a blood concentration of the alkoxyamine compound having formula I of 200 to 5000 µM. In still another variation of the embodiments set forth above, the alkoxyamine compound having formula I is administered in such an amount that the subject achieves a blood concentration of the alkoxyamine compound having formula I of 200 to 1000 µM.

In another embodiment, a method for monitoring the presence of hematopoietic and/or lymphoid tissue cancer cells in a subject is provided. In one variation, the method includes a step of obtaining a body fluid or a tissue sample from a subject suspected of having hematopoietic and/or lymphoid tissue cancer cells or a subject having been diagnosed with hematopoietic and/or lymphoid tissue cancer. The body fluid may be blood, bone marrow, cerebral spinal fluid, peritoneal fluid, or pleural fluid. Blood is found to be particularly useful. The body fluid or a tissue sample is contacted with an alkoxyamine compound having formula I to form a treated sample:

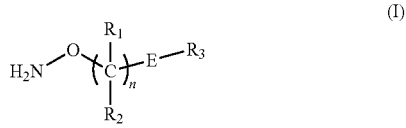

(I)

wherein:
E is

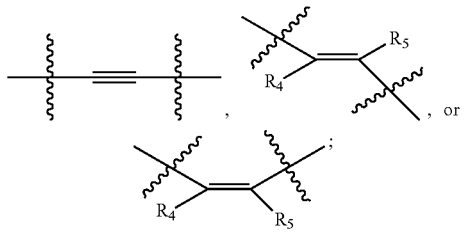

, or

Figure 7:
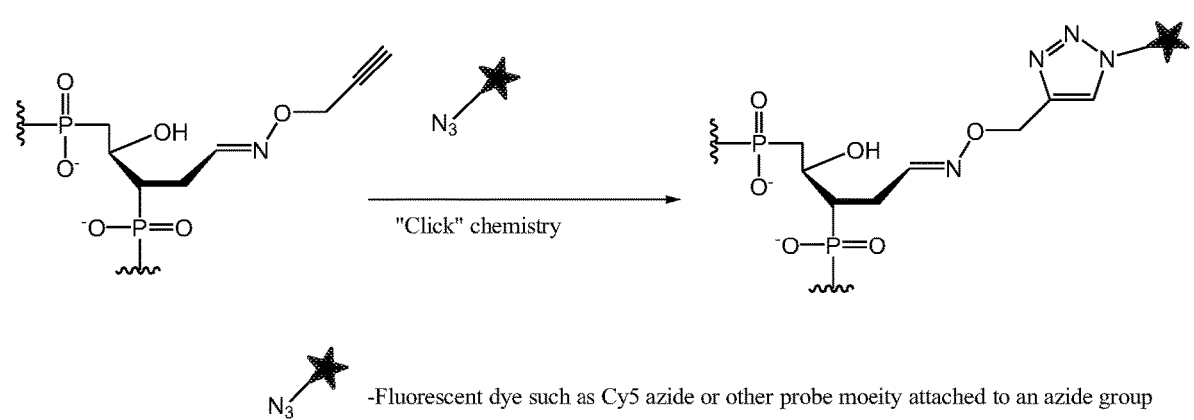
FIG. 7 is a schematic showing the attachment of an azide-containing fluorescent probe to the compounds of the invention.
Figure 9:
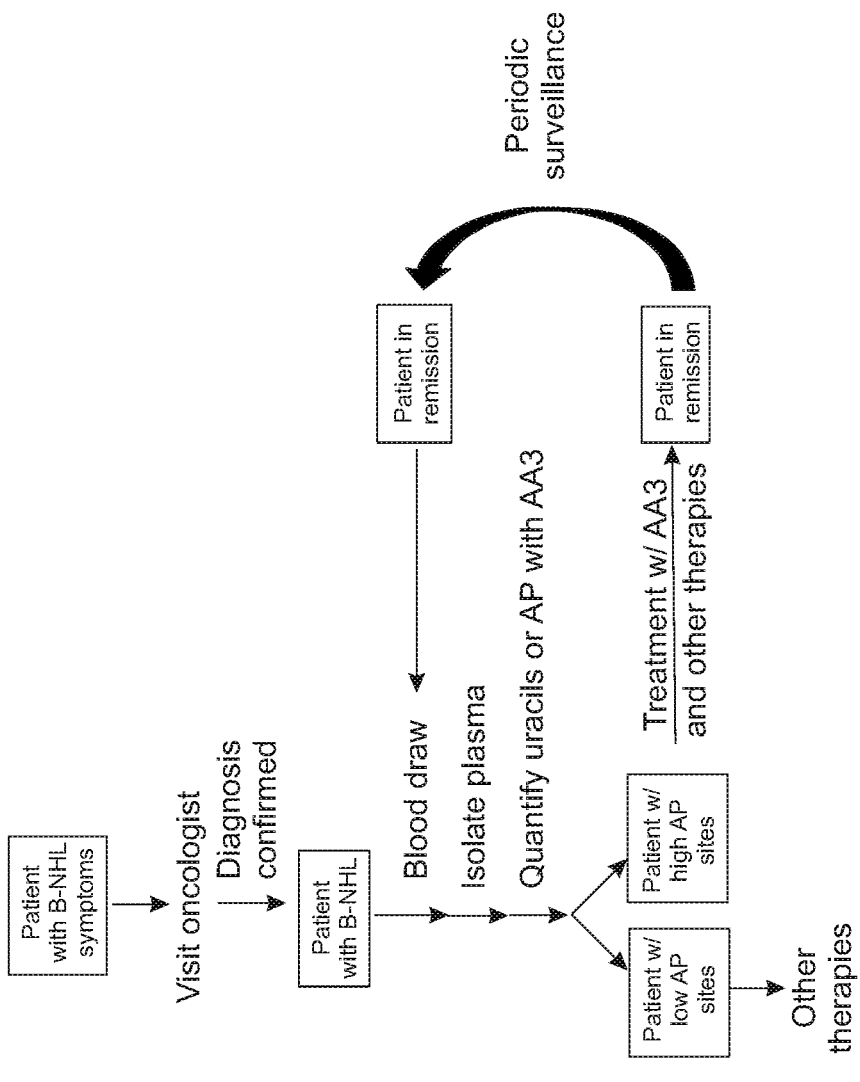
FIG. 9 is a flowchart showing a strategy for treating and monitoring B-NHL patients using AA3.

;

$R_1$, $R_2$, $R_3$, $R_4$, $R_5$ are each independently hydrogen (H), $C_{1-6}$ alkyl, F, Cl, or Br; and n is 1 to 5. In this regard, it should also be appreciated that the variations described by formulae II, IIIA and IIIB are also useful in this embodiment. DNA is then separated from the treated sample. The DNA is then contacted with a probe compound that has a probe functional group that reacts with and attaches to the E moiety of formula I to form tagged DNA. The probe compound can be used to measure the presence of and/or quantify the amount of the tagged DNA by reaction of the probe compound with the alkoxyamine compound attached to DNA and subsequent measurement of the presence or amount of the probe functional group (e.g., by fluorescence measurements using fluorescence spectroscopy). In particular, the probe compound can be used to measure the presence of and/or quantify the amount of uracils and/or AP sites. In a refinement, the probe functional group is a fluorophore. In other examples, the probe functional group is a quantum dot, a radioactive isotope, and the like. Specific examples of probe function groups include, but are not limited to, fluorescent dyes, dansyl, fluorescein and its derivatives, cyanine dyes, TAMRA and its derivatives, rhodamines and its derivatives, Alexa Fluor analogs, IR dyes, ATTO dyes, Texas Red, Oregon Green, coumarin, acridine dyes, and boron-dipyrromethene (BODIPY). In one variation, the reaction of the probe compound with the E moiety uses "click chemistry" in with an azide reacts with an alkyne as depicted in FIG. 7. Examples of azide containing probe compounds include BDP FL azide, BDP TMR azide, Coumarin 343 azide, Coumarin 343 X azide, Cyanine3 azide, Cyanine3.5 azide, Cyanine5 azide, Cyanine5.5 azide, Cyanine7 azide, Cyanine7.5 azide, FAM azide, 5-isomer, FAM azide, 6-isomer, PEP azide, Perylene azide, Pyrene azide 1, Pyrene azide 2, Pyrene azide 3, ROX azide, 5-isomer, Sulfo-Cyanine3 azide, Sulfo-Cyanine5 azide, Sulfo-Cyanine5.5 azide, Sulfo-Cyanine7 azide, TAMRA azide, 5-isomer, which are commercially available from Lumiprobe Corporation located in Hallandale Beach Fla. The quantification of uracils and/or AP sites in a subject can be used to monitor the progression of hematopoietic and/or lymphoid tissue cancers and/or decide a course of therapy thereof (FIG. 9).

In another variation, the method includes a step of obtaining a body fluid or a tissue sample from a subject suspected of having hematopoietic and/or lymphoid tissue cancer cells or a subject having been diagnosed with hematopoietic and/or lymphoid tissue cancer. The body fluid may be blood, bone marrow, cerebral spinal fluid, peritoneal fluid, or pleural fluid. Blood is found to be particularly useful. The body fluid or tissue sample is contacted with an alkoxyamine compound having formula IV to form a treated sample:

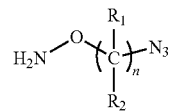

Figure 8:
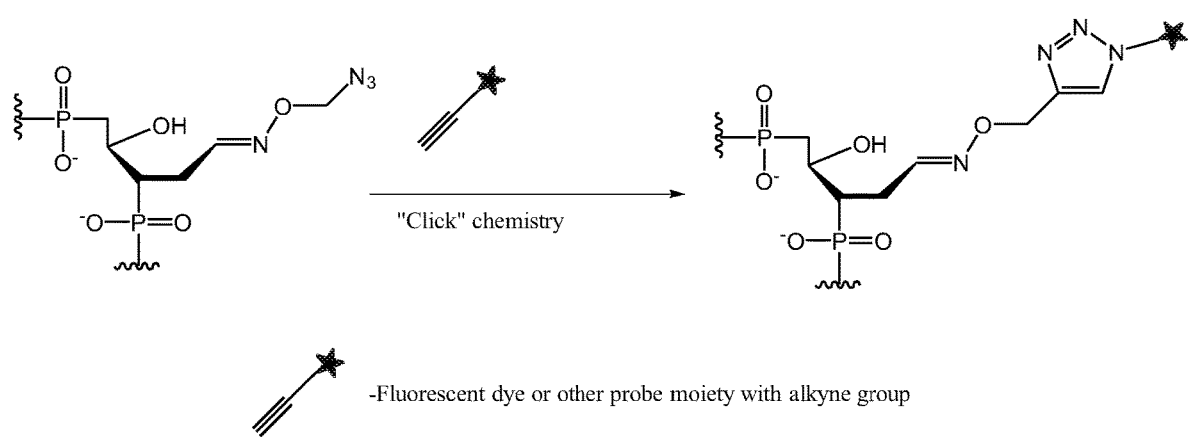
FIG. 8 is a schematic showing the attachment of an alkyne-containing fluorescent probe to the compounds of the invention.

(IV)

wherein:

$R_1$, $R_2$ are each independently hydrogen (H), $C_{1-6}$ alkyl, F, Cl, or Br; $N_3$ is an azide moiety; and n is 1 to 5. For example, $R_1$, $R_2$, are each independently hydrogen, methyl, ethyl, n-propyl, isopropyl, n-butyl, sec-butyl, isobutyl, or t-butyl. In a particularly useful variation, $R_1$, $R_2$ are each hydrogen (H). In a refinement, $R_1$, $R_2$, $R_3$ are each hydrogen (H) and n is 1 to 2. In a further refinement, n is 1. DNA is then separated from the treated sample. The DNA is then contacted with a probe compound that has a functional group that reacts with and attaches to the E moiety of formula I to form tagged DNA. In one variation, the probe compound is an alkyne-containing probe (FIG. 8). The probe compound can be used to measure the presence of and/or quantify the amount of the tagged DNA by reaction of the probe compound with the alkoxyamine compound attached to DNA and subsequent measurement of the presence or amount of the probe functional group (e.g., by fluorescence measurements using fluorescence spectroscopy). In particular, the probe compound can be used to measure the presence of and/or quantify the amount of uracils and/or AP sites. In a refinement, the probe functional group is a fluorophore. In other examples, the probe functional group is a quantum dot, a radioactive isotope, and the like. Specific examples of probe function groups include, but are not limited to, fluorescent dyes, dansyl, fluorescein and its derivatives, cyanine dyes, TAMRA and its derivatives, rhodamines and its derivatives, Alexa Fluor analogs, IR dyes, ATTO dyes, Texas Red, Oregon Green, coumarin, acridine dyes, and boron-dipyrromethene (BODIPY). Examples of useful probe molecules having an alkynyl functional group and a fluorophore include but are not limited to, 1-Ethynyl pyrene, 3-Ethynyl pyrene; BDP FL alkyne; BDP TMR alkyne; Cyanine3 alkyne; Cyanine5 alkyne; Cyanine5.5 alkyne; Cyanine7 alkyne; Cyanine7.5 alkyne; FAM alkyne, 5-isomer; FAM alkyne, 6-isomer; ROX alkyne, 5-isomer; Sulfo-Cyanine3 alkyne; Sulfo-Cyanine5 alkyne; Sulfo-Cyanine5.5 alkyne; Sulfo-Cyanine7 alkyne; and TAMRA alkyne, 5-isomer, which are commercially available from Lumiprobe Corporation located in Hallandale Beach Fla. The quantification of uracils and/or AP sites in a subject can be used to monitor the progression of hematopoietic and/or lymphoid tissue cancers and/or decide a course of therapy thereof (FIG. 9).

In variations of the embodiments set forth above, $R_1$, $R_2$, $R_3$ are each independently hydrogen, methyl, ethyl, n-propyl, isopropyl, n-butyl, sec-butyl, isobutyl, or t-butyl. In a particularly useful variation, $R_1$, $R_2$, $R_3$ are each hydrogen (H). In a further refinement, n is 1 or 2. In still another refinement, n is 1. Details for the preparation of the alkoxyamine compounds having formula I is provided in attached Exhibit A which is incorporated by reference in its entirety.

These examples illustrate the various embodiments of the present invention. Those skilled in the art will recognize many variations that are within the spirit of the present invention and scope of the claims.

Figure 10:
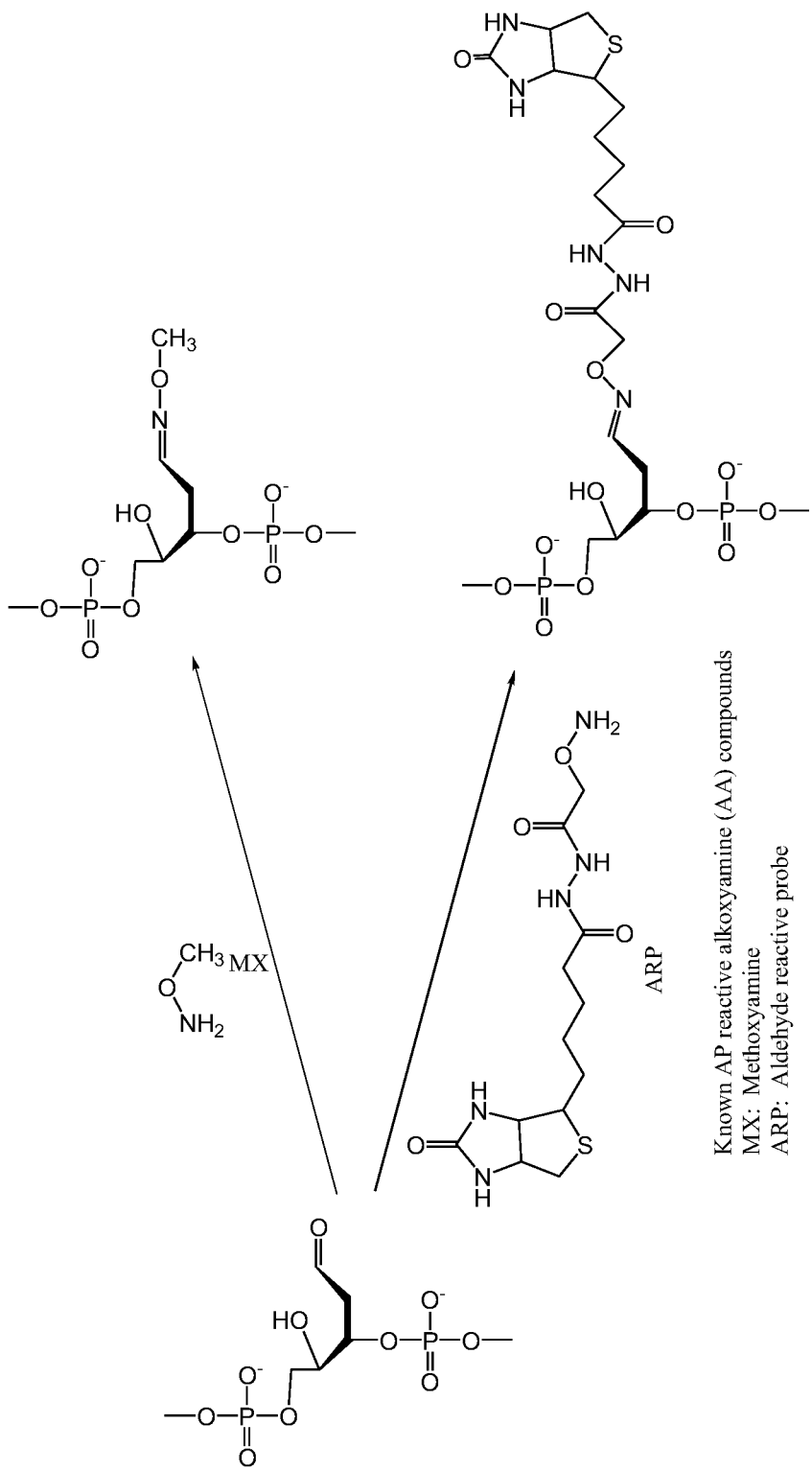
FIG. 10 is a schematic showing the reaction of known alkoxyamines with AP sites.

The starting point for the development of alkoxyamine compounds that can inhibit APE-1 and kill B-NHL cells was the two known chemicals, methoxyamine (MX) and aldehyde-reactive probe (ARP). These alkoxyamines react with the open form of the deoxyribose sugar in AP sites creating stable covalent DNA adducts (FIG. 10). Four additional chemicals, AA3 through AA7 (Table 1) that react with AP sites were synthesized in the same manner as MX and ARP. In the examples set forth below the name or abbreviations for compounds having the formula V are set forth in Table I:

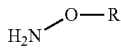

(V)

TABLE I

Alkoxyamine compounds having formula III.

| Name/designation | R Group |
|---|---|
| methoxyamine | $CH_3$ |
| AA3 | (propargyl group) |
| AA4 | (propyl group) |
| AA5 | (butynyl group) |
| AA6 | (ethyl-$N_3$ group) |
| AA7 | (allyl group) |
| ARP | (biotin hydrazide group) |

1. Cancer Cell Treatment Experiments

Figures 11A, 11B:
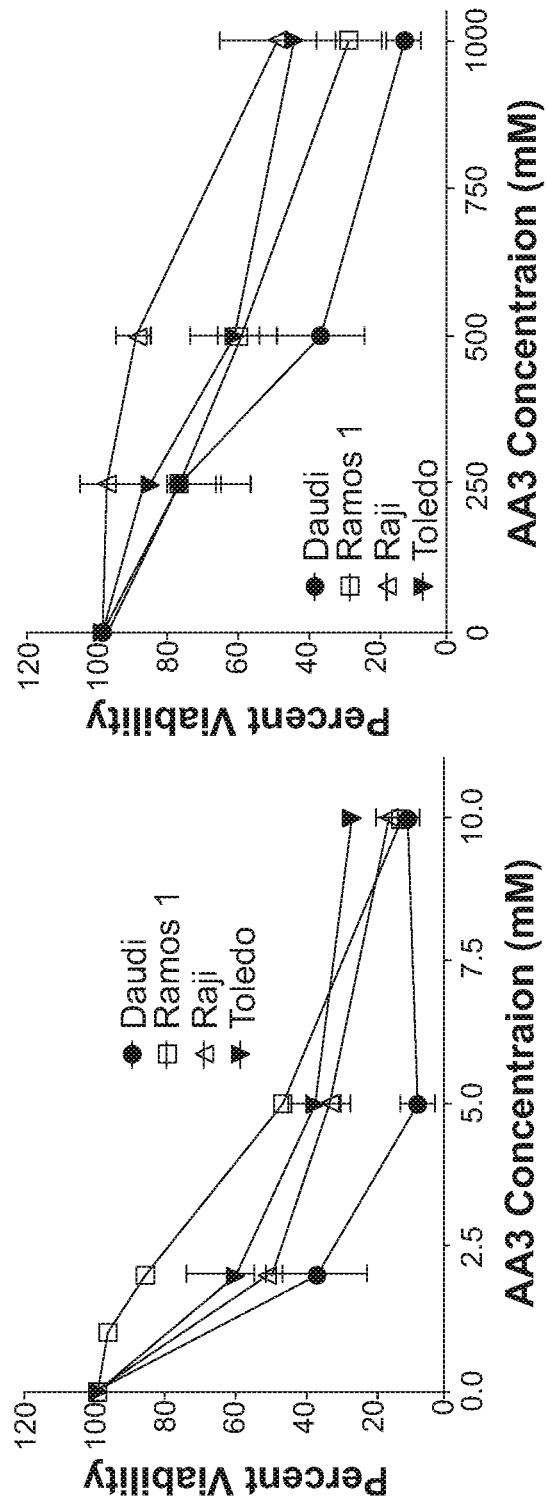
FIGS. 11A and B are plots showing that AA3 kills B cell cancer cell lines at low concentration (A) and high concentration (B).
Figures 12A, 12B:
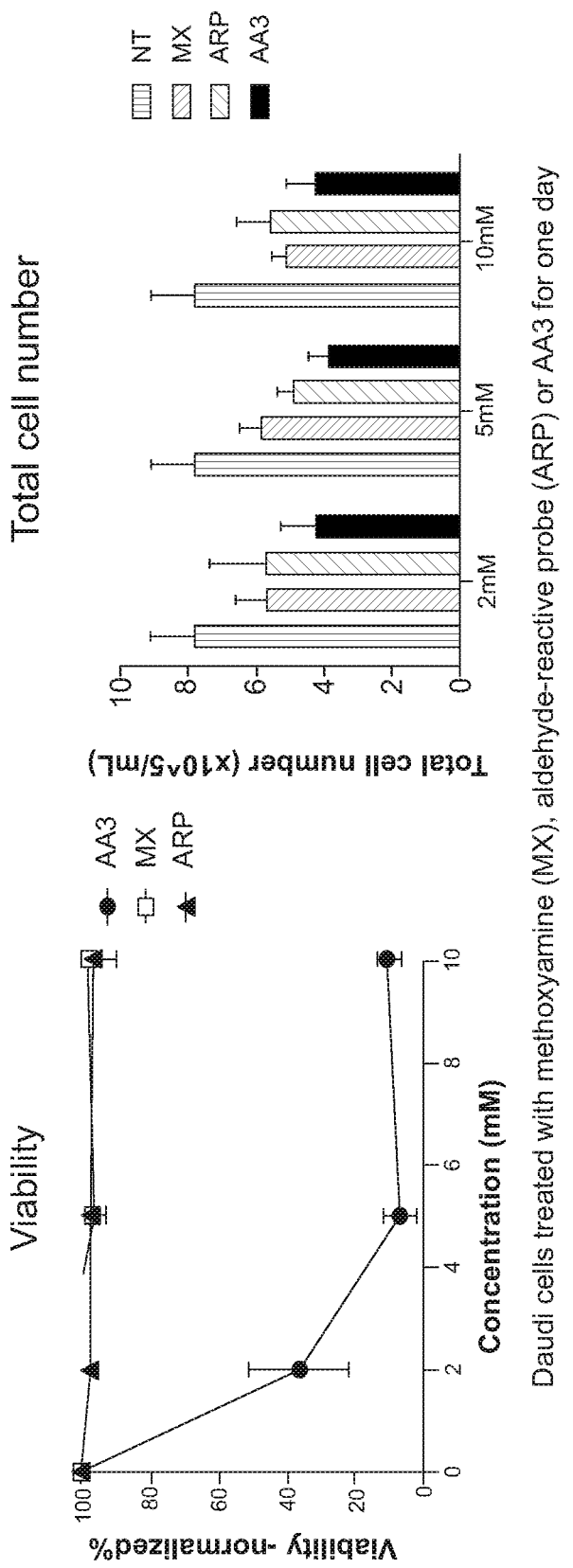
FIGS. 12A and 12B are plots (A) and bar charts (B) showing that MX and ARP are cytostatic, while AA3 is cytocidal.

When four different B-NHL cell lines were treated with AA3, all showed sensitivity to AA3 (FIG. 11). A 24 hr treatment with 1 mM AA3 killed greater than 40% cells in each culture and at 10 mM concentration, >70% cells were killed (FIG. 11). In contrast, treatment of B-NHL cells with MX or ARP did not result in cell death even at 10 mM (FIG. 12). However, treatment of these cells with MX or ARP did result in temporary pause in cell growth (FIG. 12). Therefore, AA3 cytocidal to B-NHL cells while MX and ARP are only cytostatic.

Figure 13:
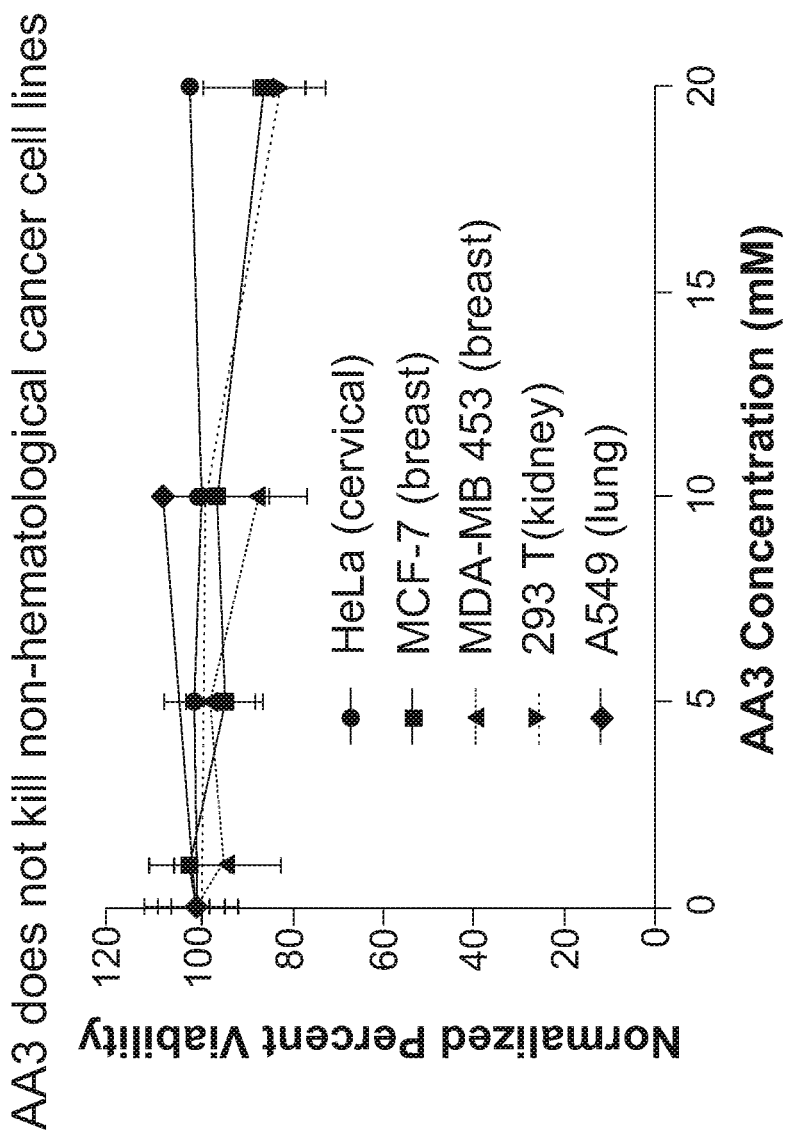
FIG. 13 is a plot showing AA3 does not kill non-hematological cancer cell lines.

When cell lines derived from five different non-hematological cancers were treated with AA3, none were very sensitive to the chemical (FIG. 13). At 10 mM none of the cells were sensitive to AA3 and some cell lines showed very modest sensitivity at 20 mM (FIG. 13). These cell lines were obtained from cancers of cervix (1 line), breast (2), kidney (1) and lung (1), and hence show that B-NHL cells are selectively sensitive to AA3.

Figure 14:
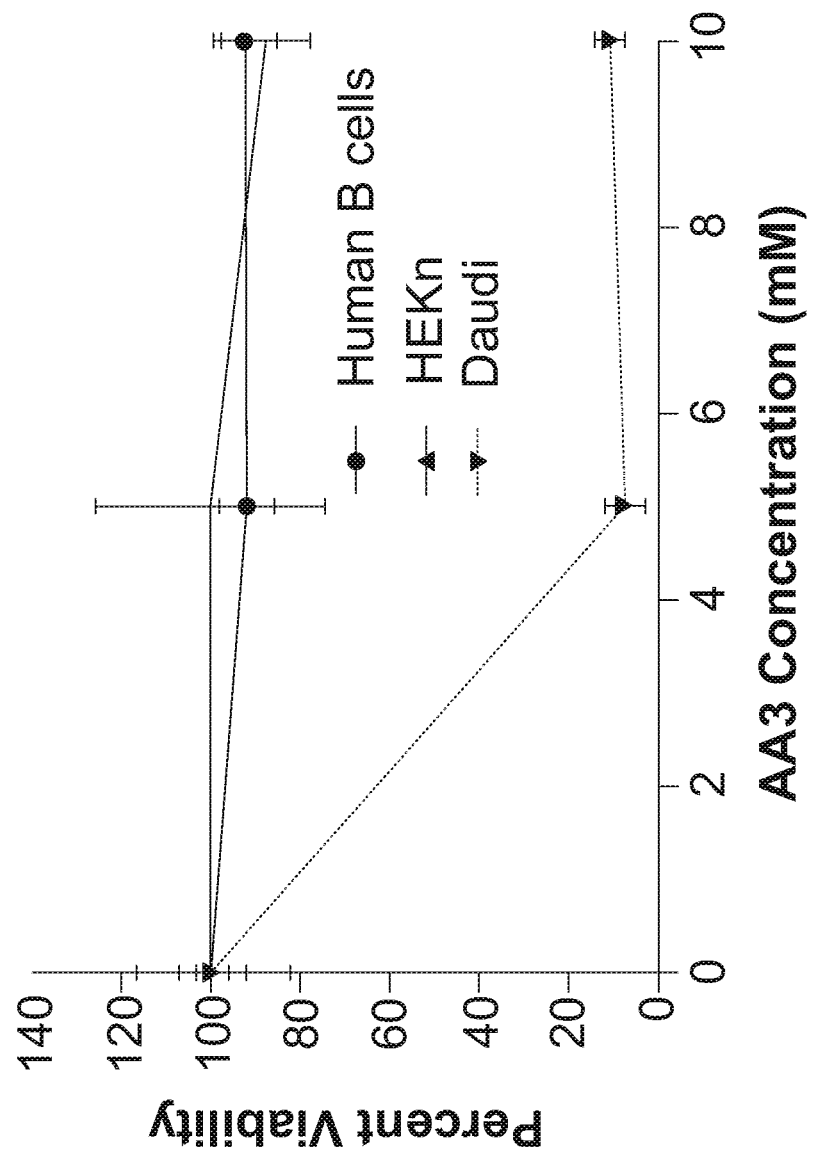
FIG. 14 is a plot showing AA3 does not kill normal cells.

Normal B and T cells were obtained from volunteer blood and stimulated to divide. The growing B and T cells were treated with AA3 and their viability was monitored. AA3 did not significantly kill normal B or T cells, while killing B-NHL cells (FIGS. 14 and 15). AA3 also did not kill primary human embryonic keratinocytes. These results show that although AA3 kills B-NHL cells, it is not cytocidal for normal human cells. We also confirmed the lack of toxicity of AA3 to normal B cells in a mouse model. We harvested spleen from normal mice and stimulated B cells in the spleen to divide using cytokines. The dividing cells were treated with AA3 and cell viability was determined. The mouse B cell lymphoma cell line CH12F3 served as a positive control. CH12F3 expresses AID and contains uracils in its genome. CH12F3 cells were also treated with AA3 and cell viability was determined. The results show that while AA3 kills CH12F3 cells, it does not kill murine splenocytes (FIG. 16).

Figure 16:
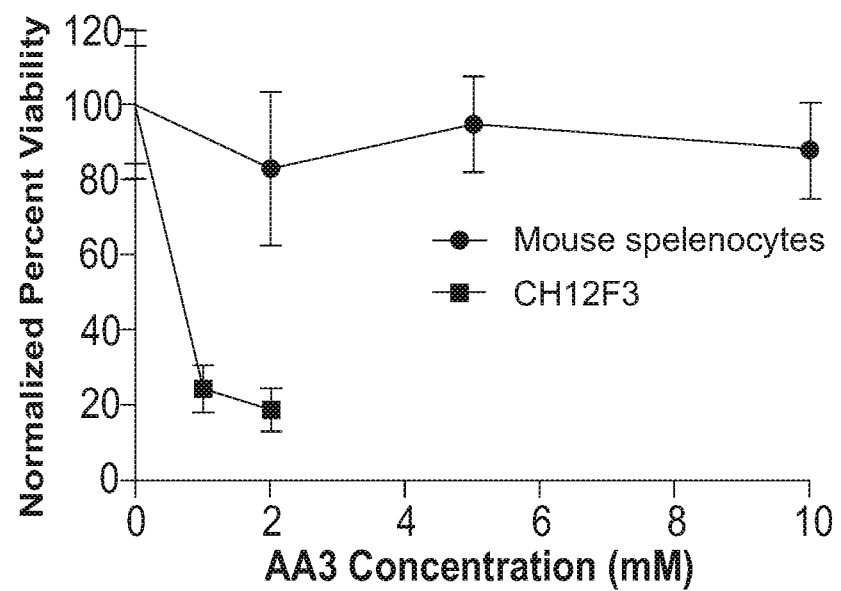
FIG. 16 is a plot comparing the killing of mouse B cell cancer cell line CH12F3 cells and normal mouse splenocytes by AA3.
Figure 17A:
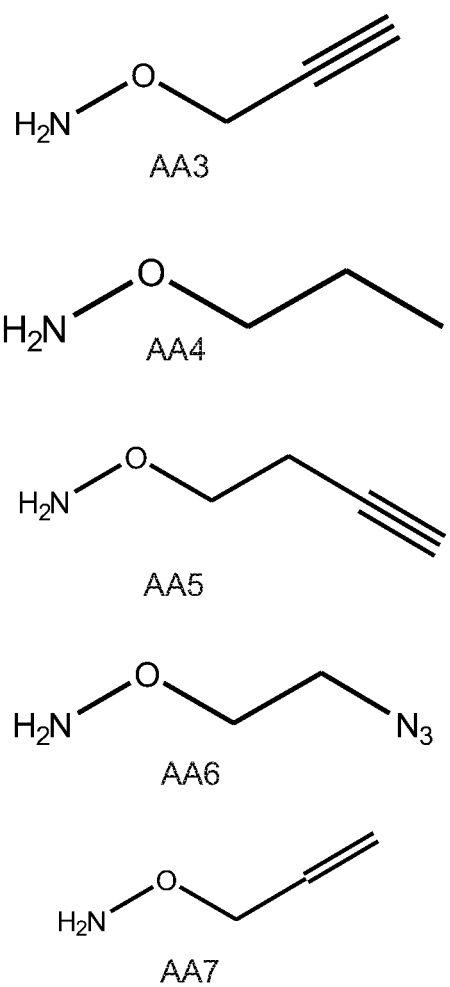
FIG. 17A provides alkoxyamines structures.
Figure 17B:
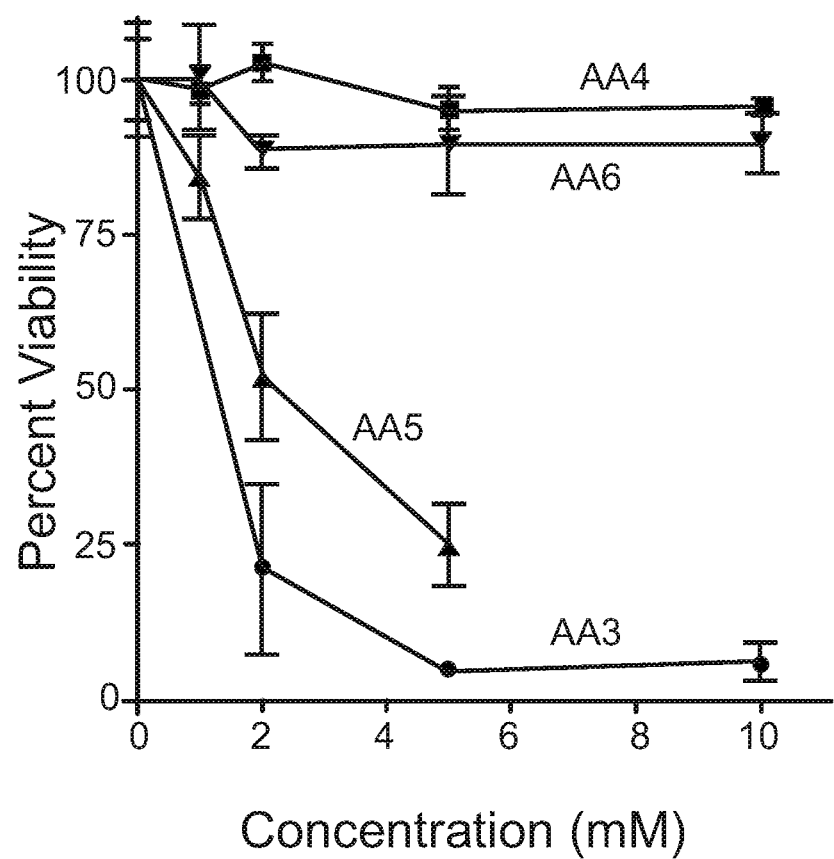
FIG. 17B is a plot showing that the alkyne functionality of AA3 is essential for cytotoxicity.
Figure 17C:
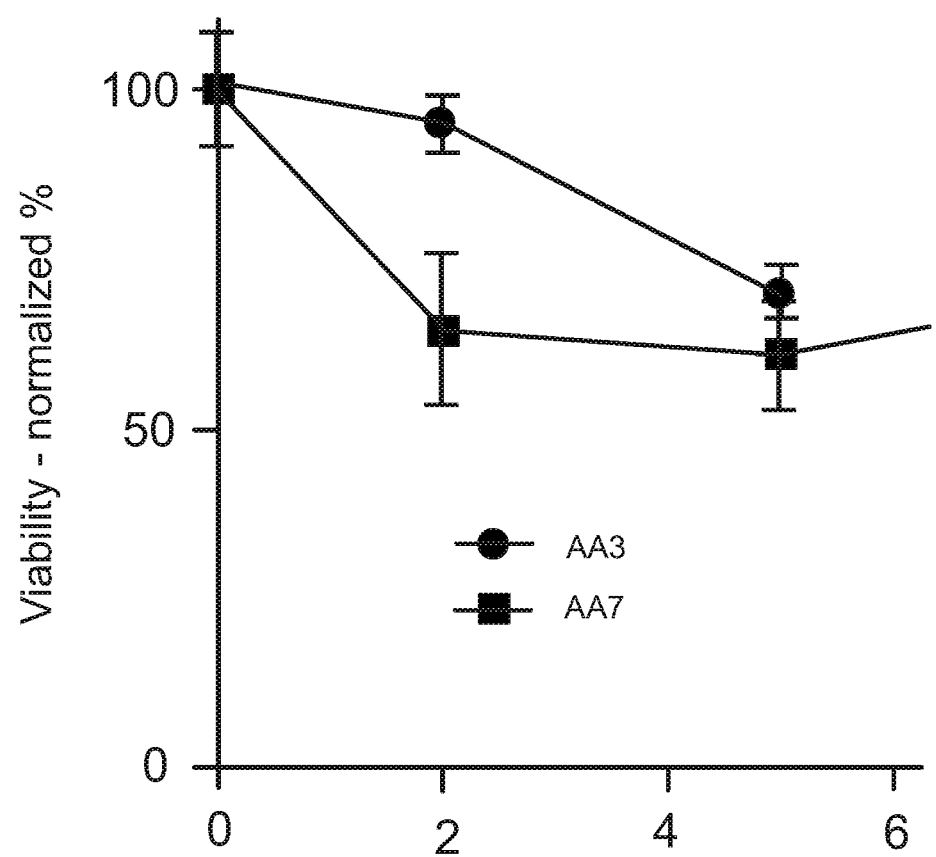
FIG. 17C is a plot showing that AA7 is cytotoxic.

When a B-NHL cell line was treated with the different alkoxyamines we developed (AA3 through AA7), only AA3 and AA5 killed these cells (FIG. 16). AA5 was somewhat less effective in killing these cells than AA3, and AA4 or AA6 did not significantly kill the cells even at 10 mM (FIG. 17). As AA3 and AA5 contain a terminal alkyne functionality while AA4 and AA6 respectively contain terminal methyl or azide group, these results show that the terminal alkyne is essential for the cytocidal action of AA3 and AA5. MX and ARP also do not contain a terminal alkyne and are not cytocidal (FIG. 12), confirming this hypothesis. AA7?

Figure 18B:
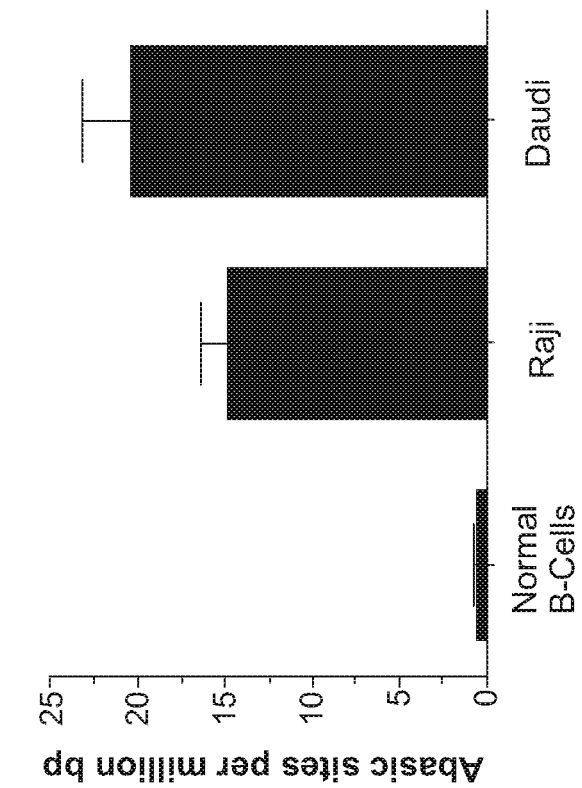
FIGS. 18A and 18B are bar charts quantifying abasic sites in normal cells and cancer cell lines.
Figure 18A:
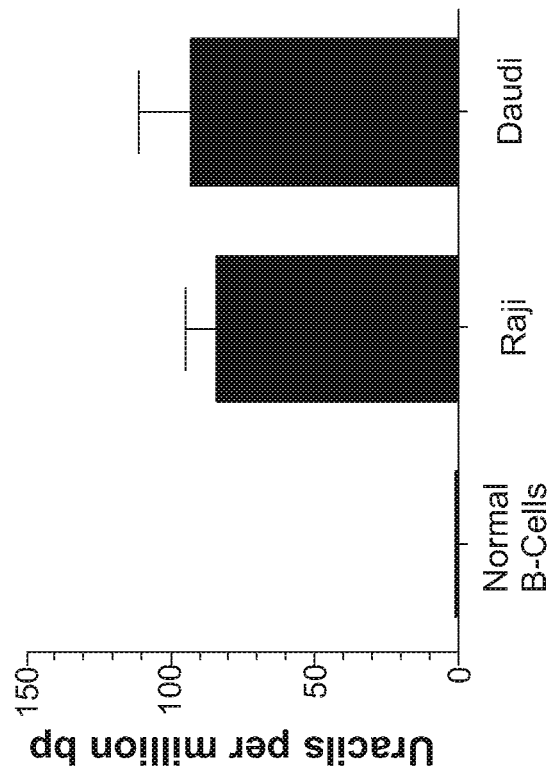

As AA3 reacts with abasic sites in DNA, a likely reason for the high sensitivity of B cell cancers to AA3 is that their genomes contain more abasic sites than normal B cell genome. We tested this hypothesis by quantifying the number of genomic uracils and abasic sites in the two B cell cancer lines that are very sensitive to AA3 and compared the numbers to those in normal blood. Normal B cells have about 1 uracil/$10^6$ bp while Raji and Daudi cells have >100 times as many uracils in their genomes (FIG. 18). Similarly, while normal blood DNA contains about 0.5 abasic sites/106 bp, Raji and Daudi cells have 30 to 40 times as many abasic sites (FIG. 18). This strongly supports the proposal that the ability of AA3 to covalently link to abasic sites in DNA is responsible for its cytotoxicity.

Figure 19:
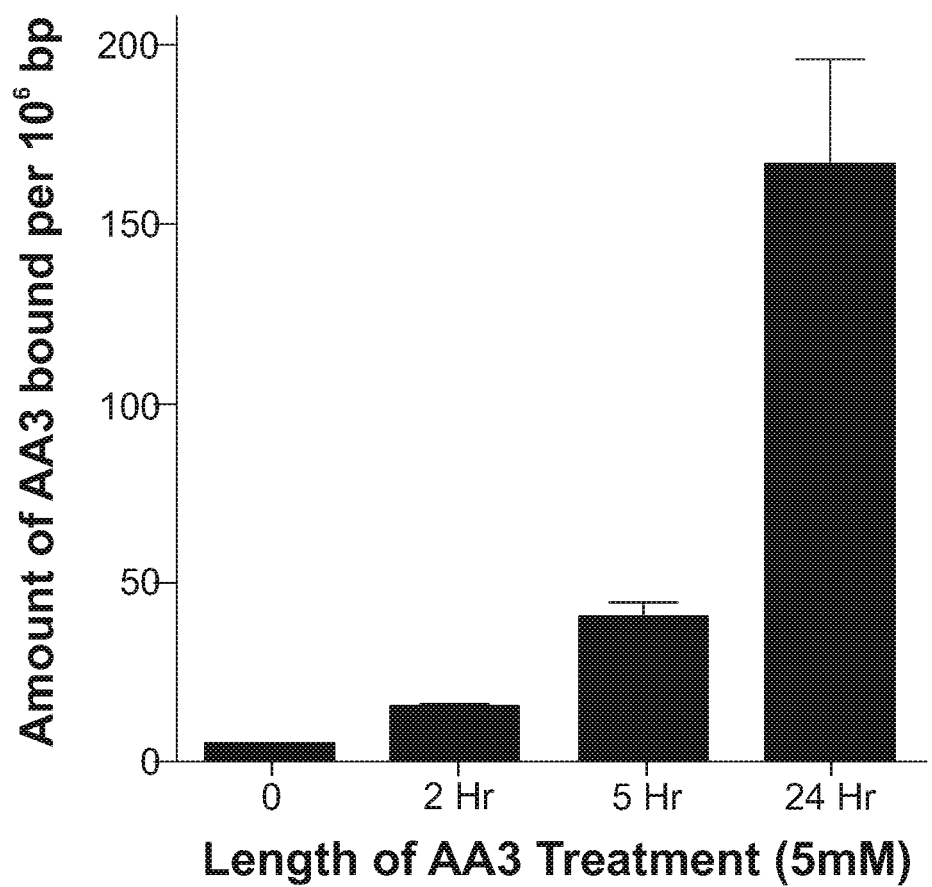
FIG. 19 is a bar chart quantifying the bonding of AA3 bound to DNA using in vivo labeling with AA3.

If AA3 kills B cell cancers because the genomes of these cells contain an excess of abasic sites then AA3 should be covalently linked to DNA of cells treated with AA3. We tested this prediction by extracting genomic DNA from Daudi cells treated with 5 mM AA3 for different lengths of time. The AA3 linked to DNA was labeled with a fluorescent tag and quantified. It can be seen that there was a time-dependent increase in the amount of AA3 covalently linked to DNA (FIG. 19). This shows that AA3 links to DNA in Daudi cells and accumulates with longer treatment.

Figures 20A, 20B:
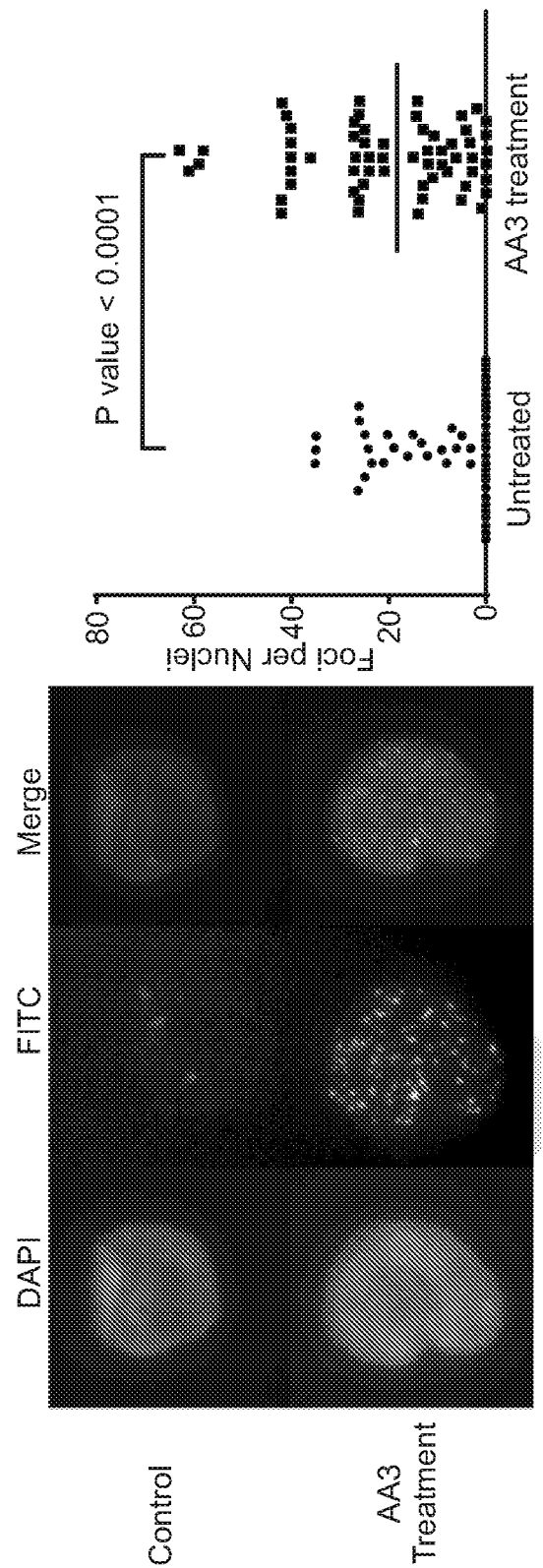
FIGS. 20A and B is a figure showing DNA strand breaks caused by AA3 as γ-H2AX foci in the nuclei of a B-NHL cell line, Daudi, (FIG. 20A) and the quantification of the number of foci per nuclei (FIG. 20B).

When cells are treated with a DNA-acting cytotoxic chemical the cause of cell death is frequently the resulting double-strand breaks in its DNA. Such breaks can be detected by immunohistochemistry using anti-γ-H2AX antibodies that detect the phosphorylation of a minor histone, H2AX. Daudi cells were treated with AA3 for 5 hours and then fixed. The cells were then bound with anti-γ-H2AX antibodies and stained with an FITC-labeled secondary antibody. As seen in FIG. 20A while the untreated cells showed few anti-γ-H2AX foci, AA3 treated cells showed a large increase in the foci. The increase in the number of foci was statistically significant (FIG. 20B).

Quantifying Abasic Sites in DNA

Figure 21:
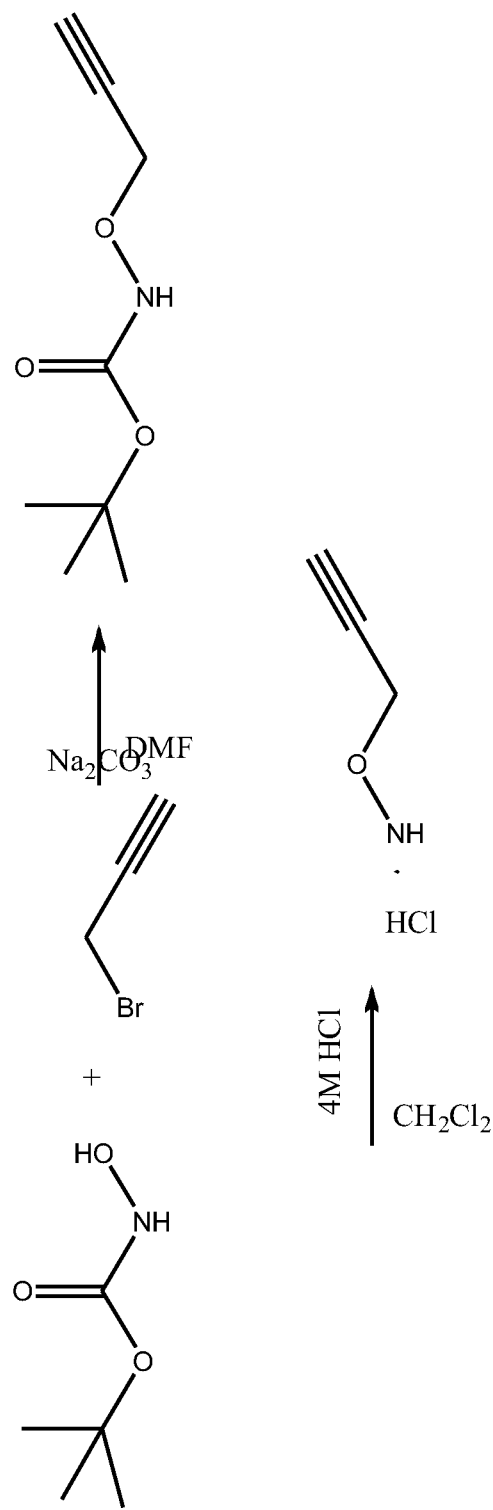
FIG. 21 provides reaction scheme showing the preparation of AA3.

2. Materials and Methods 2.1. Synthesis of O-2-propynylhydroxylamine hydrochloride (AA3) AA3 was synthesized according to Scheme 1 as set forth in FIG. 21). Propargyl bromide (11.3 mmol, Sigma-Aldrich) was added drop wise into a mixture of tert-butyl-N-hydroxycarbonate (3.7 mmol, Sigma-Aldrich) and sodium carbonate (7.4 mmol) in N,N-dimethylformamide. The reaction mixture was stirred overnight at 70° C., washed with water and extracted with ethyl acetate three times. The combined organic solution was washed with saturated aqueous sodium chloride (50 mL), dried over sodium sulfate and concentrated. The crude residue was purified by silica gel column chromatography (hexane:ethyl acetate=10:1) to give the intermediate product tert-butyl N-(2-propynyloxy)-carbamate.

HCl solution (4 M in 1,4-dioxane, 2 mL, Sigma-Aldrich) was added to a concentrated solution of tert-butyl N-(2-propynyloxy)-carbamate (2.1 mmol) in dichloromethane in an ice bath and stirred for approximately 20 min. The white precipitate was filtered and recrystallized with diethyl ether and ethanol to give O-2-propynylhydroxylamine hydrochloride (AA3, 0.08 g). Its structure was confirmed by $^1$H NMR and $^{13}$C NMR. $^1$H NMR (400 MHz, CD3OD) δ: 4.748 (s, 2H, CH2), 3.376 (t, 1H, CCH, J=2.4 Hz); $^{13}$C NMR (500 MHz, CD3OD), δ: 79.8 (CH2), 74.6 (C), 62.3 (CH).

2.2. AP Site Labeling Reaction

A 6-carboxyfluorescein-(6-FAM-) labeled oligonucleotide U-17-mer (5-6-FAM-ATTATTAUCCATTTATT-3', Integrated Device Technology) was used for the AP site labeling reaction. The oligomer (4 pmol) was incubated with E. coli uracil DNA glycosylase (UDG, 1 unit, New England Labs) at 37° C. for 30 min in reaction buffer containing 20 mM Tris-HCl (pH 8.0), 1 mM DTT and 1 mM EDTA to create AP site containing DNA. The alkoxyamine [methoxyamine, MX (Sigma-Aldrich); aldehyde reactive probe, ARP (Dojindo Laboratories) or AA3] was added into the oligomer solution at indicated concentrations, and incubated at 37° C. for another 30 min. In some experiments, the pH of the solution was adjusted with HCl or NaOH solution following removal of uracil and the pH was confirmed using pH paper. Following the reaction of alkoxyamine, unlabeled AP sites were reduced by the addition of NaBH$_4$ (Sigma-Aldrich) to 100 mM and further incubation for 5 min. If this step was omitted, we observed significant degradation of the DNA. The reactions were stopped by the addition of formamide, loading dye and heating to 95° C. for 5 min. The DNAs were electrophoresed in 20% polyacrylamide gels containing 7 M urea and scanned using a Typhoon 9210 phosphorimager (GE Healthcare). Product bands in images were quantified using ImageQuant software. In experiments involving competition between alkoxyamines, AP site containing DNA was reacted with the first alkoxyamine at 37° C. for 30 min. This was followed by the addition of the second alkoxyamine and incubation for an additional 30 min. The reactions were stopped and the products were analyzed as described above.

2.3. Click Reaction

Biotin azide [29] or Cy5 azide (Lumiprobe) was added to a solution of AA3-linked 17-mer to 0.5 mM followed by the addition of a freshly prepared solution of CuBr/TBTA (1:3 in DMSO/t-BuOH 3:1, 0.5 mM, Sigma-Aldrich). The mixture was shaken at 45° C. for 1 h. The DNAs were electrophoresed and analyzed as described above.

2.4. Genomic DNA Isolation

HeLa cells were grown in DMEM with 10% fetal bovine serum (HyClone). The cells were harvested by centrifugation and lysed by incubation for 1 h at 37° C. in Tris-EDTA buffer (TE) containing 2 μg/ml of RNase A and 0.5% SDS, followed by incubation with Proteinase K (100 μg/ml, Qiagen) at 56° C. for 3 h. The DNA was isolated by phenol/chloroform extraction and ethanol precipitation and dissolved in TE.

2.5. Creation of AP Sites in Genomic DNA by Heat and Acid Treatment

HeLa genomic DNA was digested with HaeIII (New England Bio-labs) and endogenous AP sites in DNA were reduced by the addition of NaBH$_4$ to 100 mM. The reducing agent was removed by gel filtration with MicroSpin G-25 column (GE Healthcare) and this DNA was incubated in sodium citrate buffer (10 mM sodium citrate, 10 mM NaH$_2$PO$_4$, 10 mM NaCl, pH 5.0) at 70° C. for various lengths of time (0, 15, 30, 45, or 60 min). The DNA was rapidly chilled on ice and filtered by precipitation with ethanol.

2.6. AP site quantification assay using ARP and AA3 ARP or AA3 was added to solution of genomic DNA to 2 mM and the DNA was incubated at 37° C. for 30 min. In parallel, a 75 base pair duplex DNA with one uracil (5'-T$_{37}$UT$_{37}$-3'/5'-A37GA37-3') was treated with UDG to create AP sites and was also treated with ARP or AA3. This served as an AP site standard. All DNAs were purified by phenol/chloroform extraction and ethanol precipitation, followed by MicroSpin G-25 column (GE Healthcare). The ARP tagged DNA was heated at 95° C. for 5 min, prior to transfer to a positively charged nylon membrane. The DNA was UV cross-linked to the membrane using a Beckman UV Stratalinker1800. The membrane was then incubated with Starting Block Blocking Buffer (Fisher) at room temperature for 1 h, followed by the incubation of streptavidin-conjugated horseradish peroxidase (HRP, Thermo Scientific) in blocking buffer at room temperature for 30 min. Alternatively, ARP-DNA on the membrane was incubated with 5×10-4 mg/ml of Cy5-streptavidin at room temperature for 1 h. After washing with Tris-buffered Saline containing Tween-20 (TBS-T) for 15 min, the membrane was incubated in SuperSignal West Dura Chemiluminescent Substrate (Thermo Scientific) for 5 min (when HRP-Streptavidin was used). The emitted light was captured by FluorChem Imaging System (Alpha Innotech). The resulting images were analyzed using ImageQuant software. When Cy5-Streptavidin was used, the fluorescence was quantified using Typhoon 9210 phosphorimager (GE Healthcare). AA3-tagged DNA was linked with Cy5 azide using the click reaction and purified by ethanol precipitation and filtration through a MicroSpin G-25 column (GE Healthcare). The Cy5-labeled DNA was heated at 95° C. for 5 min prior to being transferred to a positively charged nylon membrane. The membrane was scanned using Typhoon 9210 phosphorimager. All the images from chemiluminescence or fluorescence were analyzed using ImageQuant software. Alternately, the fluorescence of AA3/Cy5 tagged samples was directly measured using Synergy H1 Hybrid Reader (BioTEK) and the fluorescence intensities were obtained directly from the instrument.

2.7. AP Endonuclease Activity Assay

The cleavage activity of AP endonuclease APE-1 (1 unit, New England Biolabs) was assayed using a 6-FAM labeled oligomer (4 pmol) containing a single uracil. The uracil was excised using UDG to create an AP site and the AP site was labeled with an alkoxyamine as described above. The APE-1 reaction was per-formed in the reaction buffer (50 mM potassium acetate, 20 mM Tris-acetate, 10 mM magnesium acetate, 1 mM DTT, pH 7.9) at 37° C. for 1 h. DNA products were stabilized by incubation with NaBH4 and analyzed by gel electrophoresis as described above.

2.8. Killing of HeLa Cells by a Combination of MMS and MX or AA3

Methyl methanesulfonate (MMS, Sigma-Aldrich) was diluted in phosphate buffered saline. MX or AA3 was dissolved in sterile water, and the pH was adjusted to 7 using NaOH solution. The solutions of all the chemicals were freshly prepared for each cytotoxicity experiment. HeLa cells were seeded in 48-well tissue culture plates at $3 \times 10^4$ to $6 \times 10^4$ cell/mL and grown overnight in DMEM with 10% fetal bovine serum (HyClone). Cells were treated with MMS or as a combination of MMS with MX or AA3 at indicated concentrations and harvested after 24 h. The viability of the cells was assessed via trypan blue (HyClone) exclusion assay performed using TC20 Automated Cell Counter (Bio-Rad Laboratories).

3. Results and Discussion 3.1. Design and Synthesis of AA3

Methoxyamine (MX) and aldehyde-reactive probe (ARP) are well-known chemicals that react with AP sites. While MX does not allow tagging of AP sites, ARP is bulky, contains biotin as the only tag and requires proteins and enzymes for its use [8, 10]. To create a more versatile agent for labeling AP sites with good reactivity, we synthesized a small alkoxyamine with alkyne functionality (see Section 2). This chemical, AA3 should react with AP sites in the same manner as MX, but should allow facile labeling of the sites with different biochemical tags using copper-catalyzed azide-alkyne cycloaddition reaction (click chemistry). AA3 should be useful for intracellular labeling of AP sites in addition to in vitro DNA labeling, because click chemistry is considered bioorthogonal [30, 31].

3.2. Labeling of AP Sites Using AA3

Figure 22A:
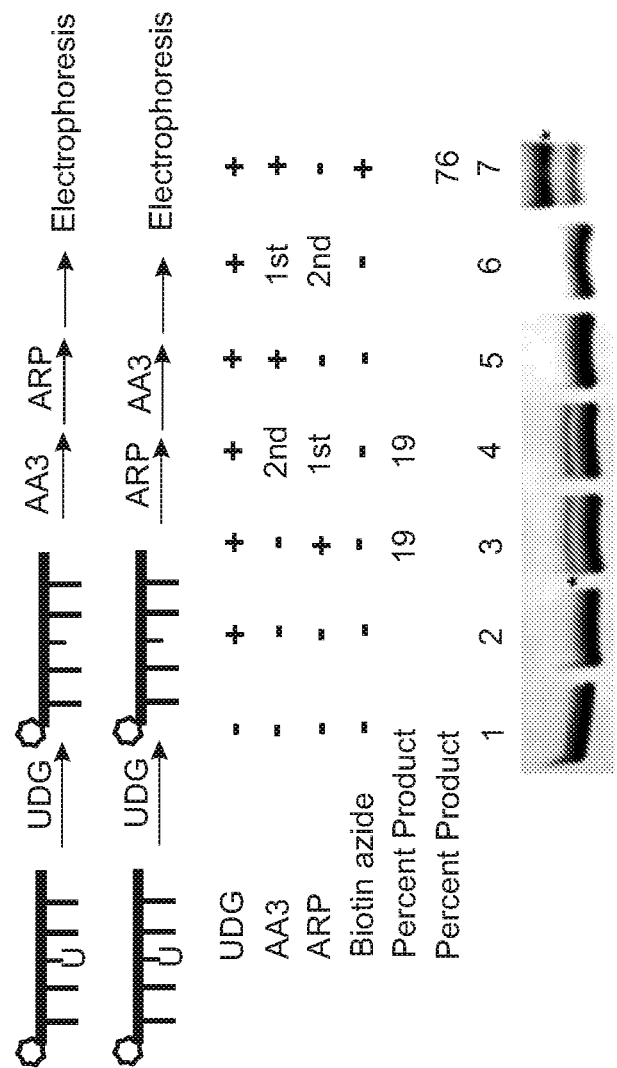
FIGS. 22A, 22B, and 22C. Reactivity of AA3 towards AP sites in DNA. A scheme for each experiment is shown at the top of each part of the figure. (A) Inhibition of ARP reaction by AA3. Briefly, a 5'-6-FAM labeled DNA was incubated with UDG to create AP sites and reacted with AA3 and ARP in the indicated order. For the reaction in lane 7, DNA was incubated with UDG and AA3, followed by reaction with biotin azide using click chemistry. Asterisks (*) mark both the 17-mer+ARP and 17-mer+AA3+Biotin bands. (B) Comparison of reactions of AA3 with AP sites in double-stranded DNA (lane 3 and 4) and single-stranded DNA (lane 7 and 8). Reactions of ARP with double- and single-stranded DNA are shown in lanes 2 and 6, respectively. (C) Labeling of AP sites with Cy5 using AA3. AP sites were reacted with AA3 followed by click reaction with biotin azide (lane 3) or Cy5 azide (lane 4).
Figure 22B:
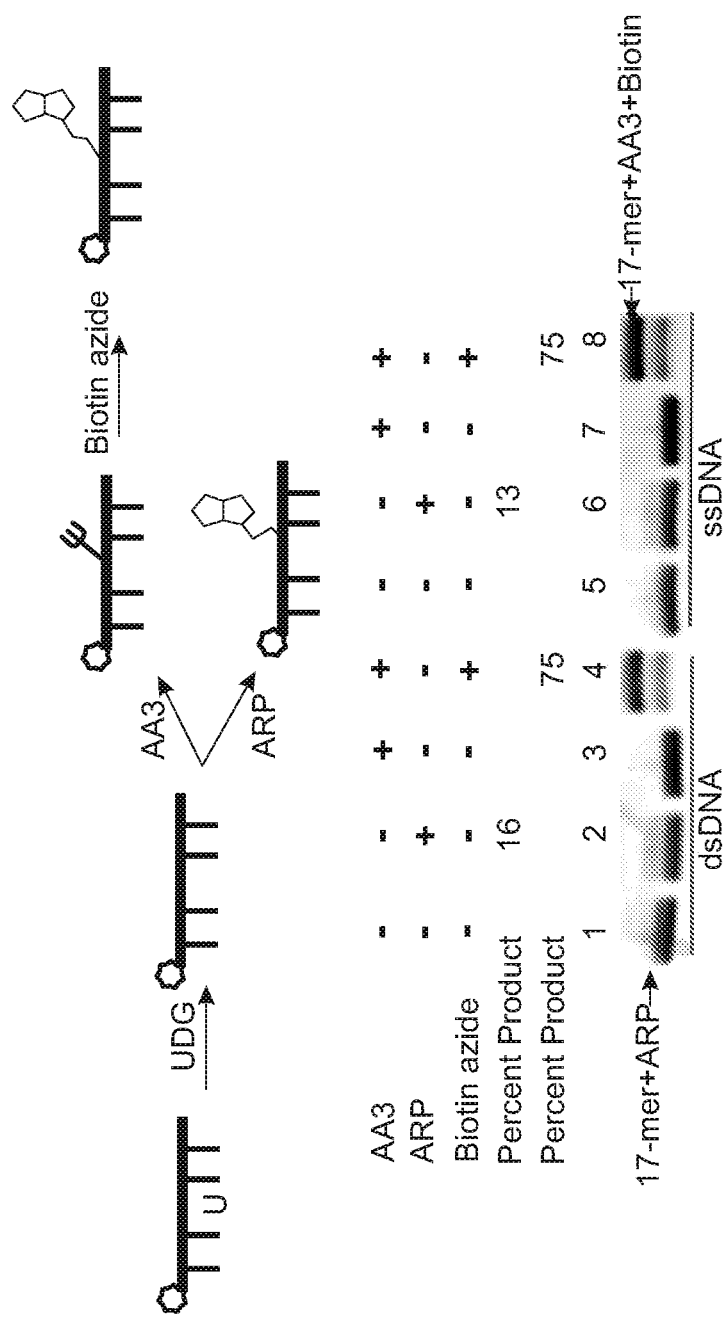

To demonstrate that AA3 reacts with AP sites we showed that it inhibits the ability of ARP to label AP sites. AP sites were created by the excision of uracils by uracil-DNA glycosylase (UDG) in a synthetic oligomer. They were reacted with ARP and the products separated on a denaturing gel. The linking of ARP to DNA caused a shift in mobility of oligomer (FIG. 22A; lane 3; [23]). This shift was eliminated completely if the AP sites were pretreated with AA3 (FIG. 22A; lane 6). This shows that AA3 forms a stable adduct at AP sites and blocks the reaction of ARP. Treatment of the oligomer with AA3 alone did not create an observable shift in oligomer mobility (FIG. 22A; lane 5) probably because of the small size of AA3 compared to ARP (MW 71.0 vs. 331.4). However, treating the oligomer with the two chemicals in the reverse order still created the mobility shift (FIG. 22A; lane 4) suggesting that ARP-DNA adducts are stable and cannot be replaced with AA3. AA3 is both versatile and more efficient than ARP in labeling AP sites. AP sites reacted with AA3 can be labeled with an appropriate azide using click chemistry. Following a reaction with AA3, biotin azide was used to routinely convert greater than 70% of the AP sites to biotinylated form (FIG. 22A, lane 7). It may be possible to increase the reaction yield through further optimization of the click reaction [32-34]. Prior treatment of the AP sites with a reducing agent, sodium borohydride, eliminated labeling showing that AA3 reacts with only the unreduced form of the AP site. AA3 reacted equally well with AP sites in ssDNA and dsDNA converting overwhelming majority of substrate to product (FIG. 22B). In contrast, ARP converted less than 20% of the substrate to biotinylated product (FIG. 22A, lane 3, FIG. 22B, lanes 2 and 6).

Figure 22C:
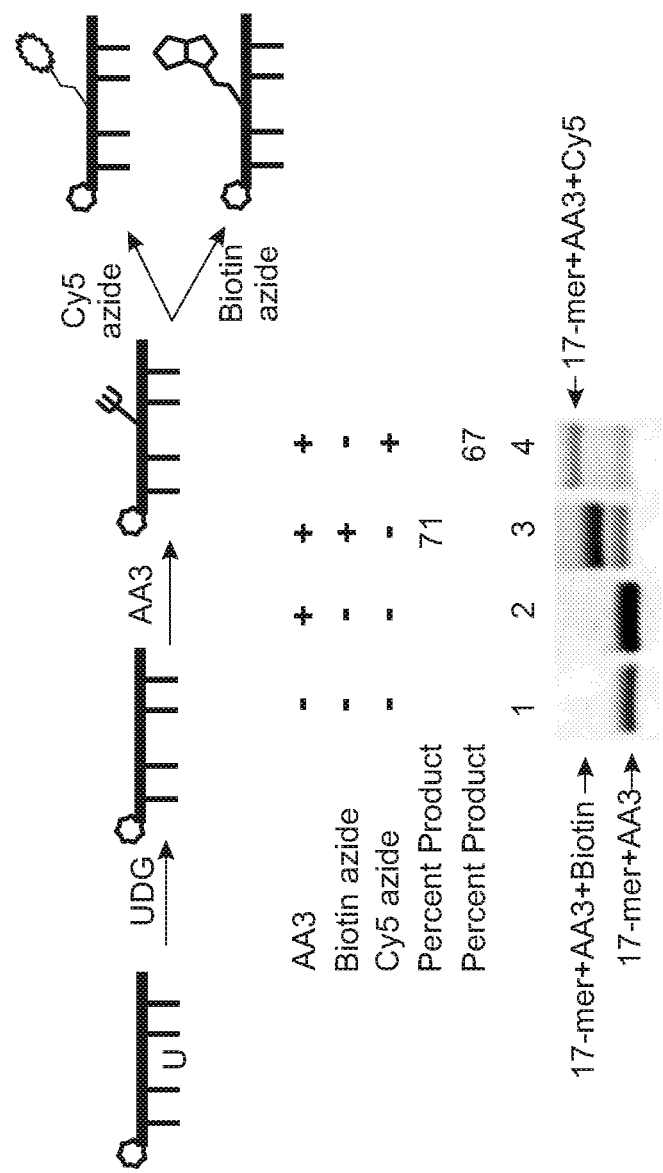

To show that AA3 can be also used to label AP sites with different tags, we replaced biotin azide with Cy5 azide in the click chemistry. Using this strategy 67% of AP sites in the oligomer were labeled with the fluorescent label (FIG. 22C, lane 4). As a large number of fluorescent dyes and other molecules are commercially available in azide form, it should be possible to choose appropriate labels for AP sites based on the intended application.

3.3. AA3 has Better Reactivity Profile than ARP

We were surprised that ARP labeled <20% AP sites under the standard conditions (Tris buffer, pH 8.0). To investigate this, the pH of the reaction buffer was changed after uracil excision, but prior to addition of ARP. When the products were quantified by gel electrophoresis the gel showed that ARP reacts well with AP sites only at acidic conditions (FIG. 23A). We consistently found that with 0.2 µM oligomer and 5 mM ARP, <20% of the substrate was converted to product at pH 7 or 8 (FIGS. 22 and 23A). In contrast, AA3 was much more reactive with AP sites over the pH range of 4 to 8, and converted 57% or greater AP sites to AP-AA3 adduct (FIGS. 22 and 23B). Therefore, AA3 is more suitable for in situ labeling of AP sites in cells than ARP.

Under physiological conditions, AA3 was more reactive toward AP sites than ARP even at much lower concentrations. Increasing the ARP concentration from 5 to 10 mM resulted in an increase in product formation from 13 to 20% (FIG. 24A), while AA3 converted greater than that amount of substrate to product even at 1 mM (FIG. 24B). The results from three independent experiments are presented in FIG. 24C. They show that AA3 was much more reactive at pH 7 toward AP sites than ARP over a range of concentrations and AA3 was about as reactive toward AP sites at 1 mM as ARP was at 10 mM (FIG. 24C).

3.4. AA3 can be Used to Quantify Genomic Aldehydic Lesions and AP Sites

Figure 25A:
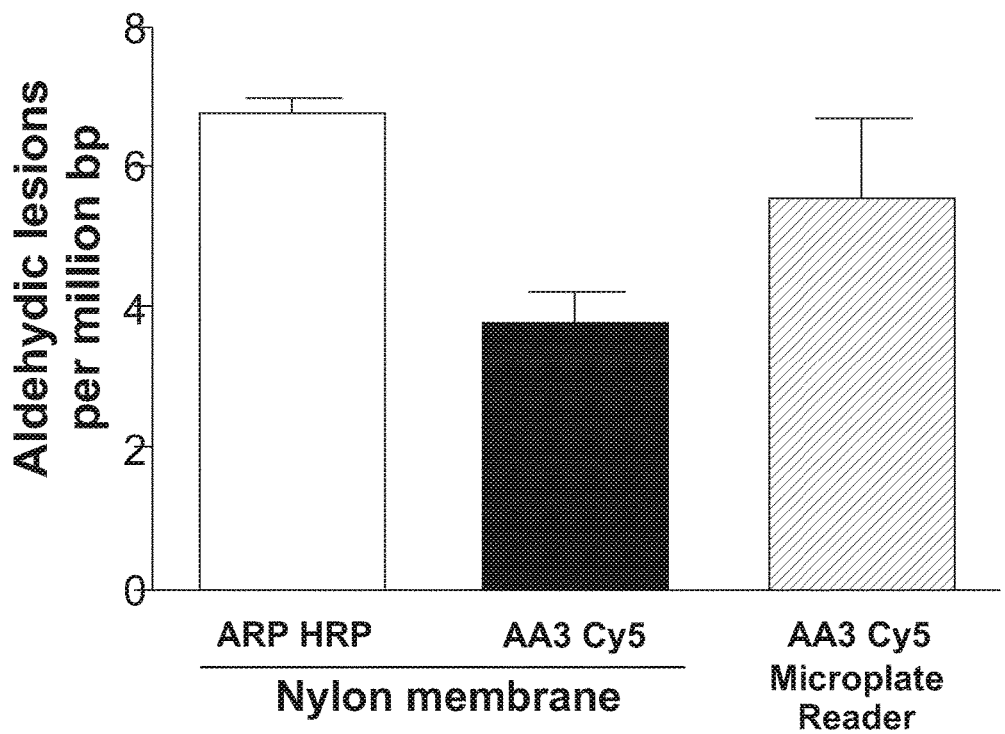
FIGS. 25A and 25B. Quantification of aldehydic lesions and AP sites using ARP and AA3. (A) HeLa DNA was labeled with ARP and vacuum-spotted onto a nylon membrane. Aldehydic lesions in this DNA were quantified using streptavidin-conjugated horseradish peroxidase (HRP) and detected using a chemiluminescent substrate (open bar). In parallel, aldehydic lesions in HeLa DNA were also labeled with AA3 followed by reaction with Cy5 azide and quantification of fluorescence on a nylon membrane (black bar). AA3-labeled aldehydic lesions reacted with Cy5 azide were also quantified in solution using a microplate reader (gray bars). Mean and standard deviation of triplicate samples is shown. (B) HeLa DNA was pre-treated with $NaBH_4$ to reduce endogenous aldehydic lesions and AP sites were generated by heat and acid treatment for different lengths of time. The AP sites were labeled using ARP or AA3 for labeling and the DNA was spotted onto a nylon membrane and the membranes scanned to quantify AP sites (Left). AP sites in the same DNAs were also quantified by reacting them successively with AA3 and Cy5 azide, and measuring fluorescence intensity directly using a microplate reader (right). Mean and standard deviation of triplicate samples is shown for each time point.
Figure 25B:
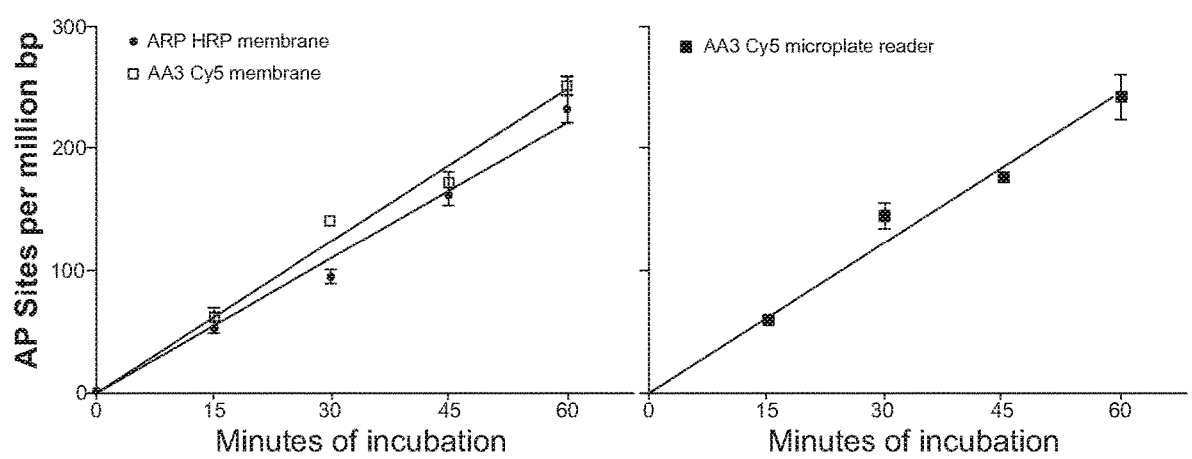

As ARP has been used to quantify AP sites in genomic DNA of normal cells [11, 16, 17] and cancer cell lines [16, 35], we wished to compare the use of AA3 in a similar setting. The comparison was done in three different ways. First, genomic DNA was extracted from HeLa cells and the AP sites were quantified using ARP or AA3. When ARP was used, the DNA adducts were quantified using streptavidin-conjugated horseradish peroxidase [16], and when AA3 was used the adducts were tagged with Cy5 for quantification. In both cases, the samples were spotted on a nylon membrane using a dot-blot apparatus and the light or fluorescence from each dot was quantified. It should be noted that ARP and AA3 would react with all aldehydic lesions in DNA including intact unoxidized AP sites, cleaved AP sites and formamidepyrimidines which result from alkylation or oxidation of purines in DNA [16, 36]. Such lesions occur routinely in cellular DNA, and hence the sites labeled by ARP or AA3 in HeLa DNA are referred simply as aldehydic lesions in Dante results from these experiments are shown in FIG. 25. The ARP-based method gave about twice as many aldehydic lesions in HeLa as AA3 (FIG. 25A). A previous study of HeLa DNA using ARP reported (35) somewhat higher number of aldehydic sites (~20 per $10^6$ bp). The differences in those numbers and the numbers obtained in our study may be due to methods of DNA preparation, age of DNA used and use of different AP site standards. The Mendez et al. study used depurinated pBR322 as the standard (35), while we used a synthetic oligomer containing uracil that was treated with UDG as the AP site standard. In a second set of experiments, HeLa DNA was first treated with sodium borohydride to reduce preexisting aldehydic lesions and make them resistant to ARP or AA3. The DNA was then heated under acidic conditions to create new AP sites through depurination. The depurination reaction was terminated at various times and the AP sites were quantified using the two chemicals as described above. The data showed there was a linear time-dependent increase in the number of AP sites and the two methods gave comparable numbers for AP sites at all time points (FIG. 25B, left panel).

3.5. Sensitivity and Ease of Use of AA3

To determine whether AA3-based quantification of AP sites was as sensitive as ARP-based quantification, we treated different amounts of a DNA oligomer containing AP sites with ARP or AA3 and quantified the products. The membrane images from the two parallel experiments are shown in FIG. 26A. The sample containing $10^9$ AP sites was visible using ARP-chemiluminescence assay, but the sample with $10^8$ sites could not be detected above background. In contrast, $10^8$ AP site sample could be detected in the image from AA3-fluorescence assay. Adjusting the image brightness did not change the relative sensitivities of AA3 and ARP. The membrane containing ARP-labeled samples has much higher background than the membrane with AA3-labeled samples. Thus under these conditions, AA3-based detection of AP sites has lower background and greater sensitivity than ARP. However, the readout for the comparison of two techniques used to quantify AP sites in FIG. 26A were different, and we wanted to eliminate this variable in the comparison. To accomplish this we labeled different amounts of the AP site-containing DNA duplex with ARP and then bound it to Cy5-streptavidin. In parallel reactions the DNA was reacted with AA3 followed by reaction with Cy5 azide. Both sets of samples were spotted on nylon membranes and Cy5 fluorescence was quantified. The results show that both methods result in a linear relationship between the number of AP sites and Cy5 fluorescence (FIG. 26B), but the use of AA3 results in lower background and hence greater signal-to-noise ratio (FIG. 26B, inset). One problem of using ARP to quantify AP sites is the difficulty of separating unbound protein (HRP or streptavidin) from protein that is bound to DNA. This is the likely source of the high back-ground seen in membranes with ARP-DNA (FIG. 26). In contrast, AA3-based method does not use a protein and hence it is possible to eliminate unreacted Cy5 azide from the much larger Cy5-AA3-DNA using a G-25 mini-column. The Cy5 fluorescence can then be directly measured using a microplate fluorometer. We performed this simplified procedure on endogenous aldehydic lesions in HeLa DNA and on AP sites created by heat and acid treatment, and the results were comparable to those obtained by the other two methods (FIGS. 25A and B, right panel). Thus, use of AA3 simplifies AP site quantification.

3.6. AA3 Inhibits APE-1

Figure 27A:
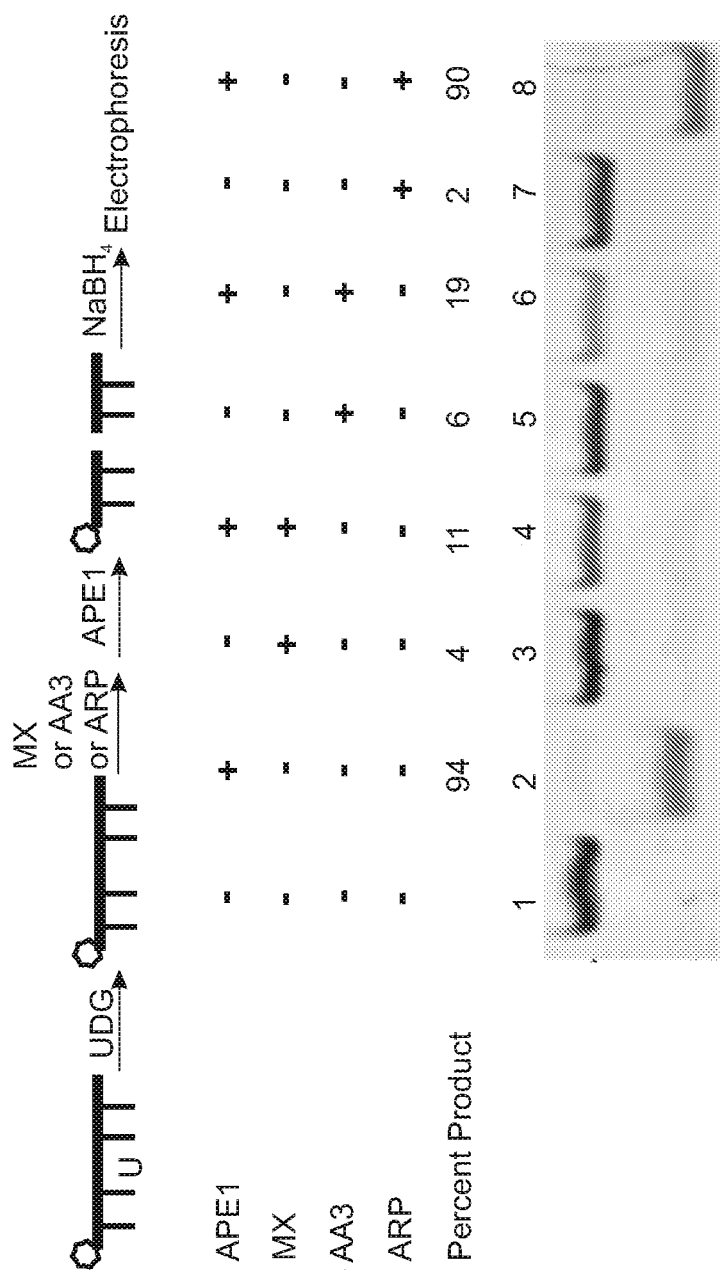
FIGS. 27A and 27B. Inhibition of APE-1 activity by MX, ARP or AA3. A scheme for each experiment is shown at the top of each part of the figure. (A) DNA containing an AP site was reacted with MX, AA3 or ARP at pH 7. This was followed by incubation of DNA with APE-1. (B) DNA containing an AP site was reacted with MX, AA3 or ARP at pH 5. This was followed by incubation of DNA with APE-1.
Figure 27B:
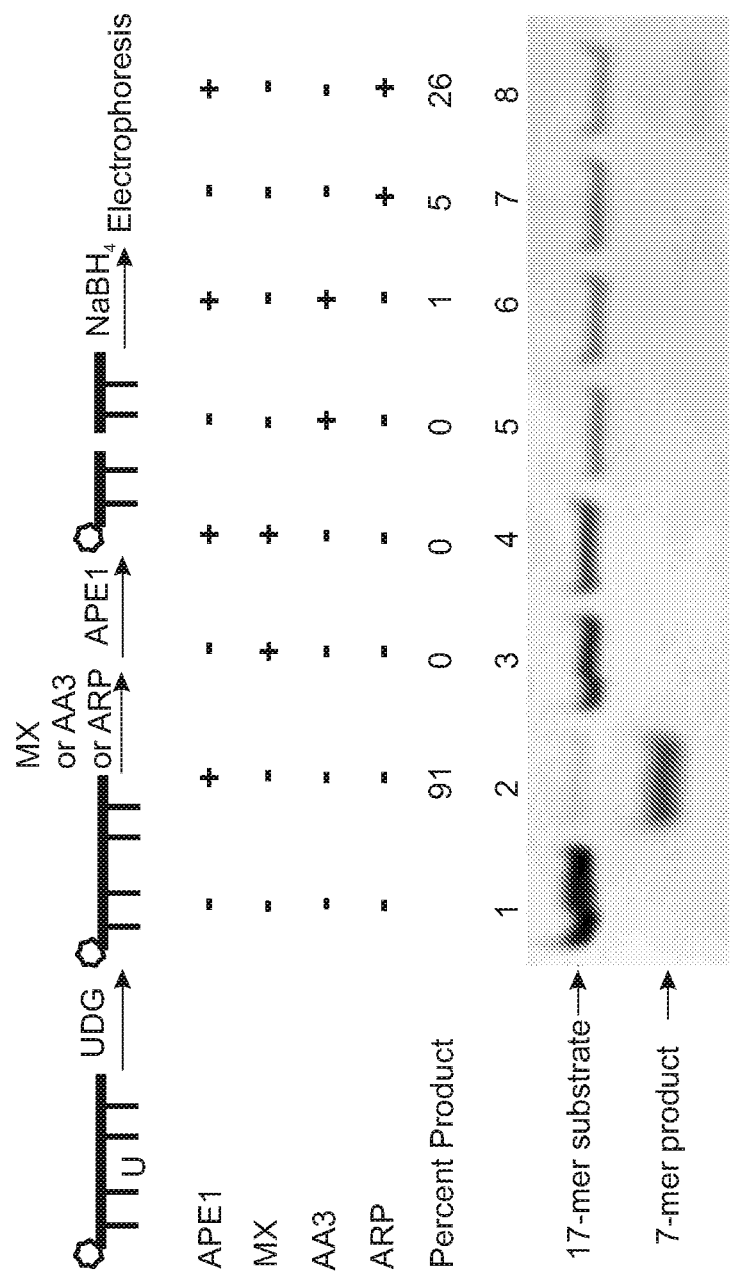

The reaction of MX with AP sites is known to inhibit its repair by AP endonuclease [37] and this is the basis of its proposed use as part of anti-cancer combination chemotherapy [24]. To find out whether ARP and AA3 similarly inhibit AP endonuclease APE-1, we reacted an oligomer containing an AP site with MX, ARP or AA3 and then challenged the DNA with APE-1. The results showed that while MX and AA3 were very effective in blocking action of APE-1, ARP was a poor inhibitor of the enzyme under physiological condition. When AP sites were reacted with ARP at pH 7 and the DNA was then treated with APE-1, about 90% of the DNA was cleaved by the enzyme showing poor protection of AP sites by ARP (FIG. 27A, lane 8). This is probably because of the poor reactivity of ARP at pH 7 (FIG. 24A). In contrast, both MX and AA3 protected an overwhelming majority of AP sites at pH 7 (FIG. 27A, respectively lanes 4 and 6). When the pH of ARP reaction was lowered to 5, protection of AP sites against cleavage by APE-1 increased to 74% (FIG. 27B, lane 8). Under the same conditions, the protection by MX and AA3 was ~100% (FIG. 27B, lanes 4 and 6). Thus, MX and AA3 protect AP sites against APE-1 cleavage equally well at both pH conditions.

3.7. AA3 Kills Cells Containing DNA Base Damage

Figure 28A:
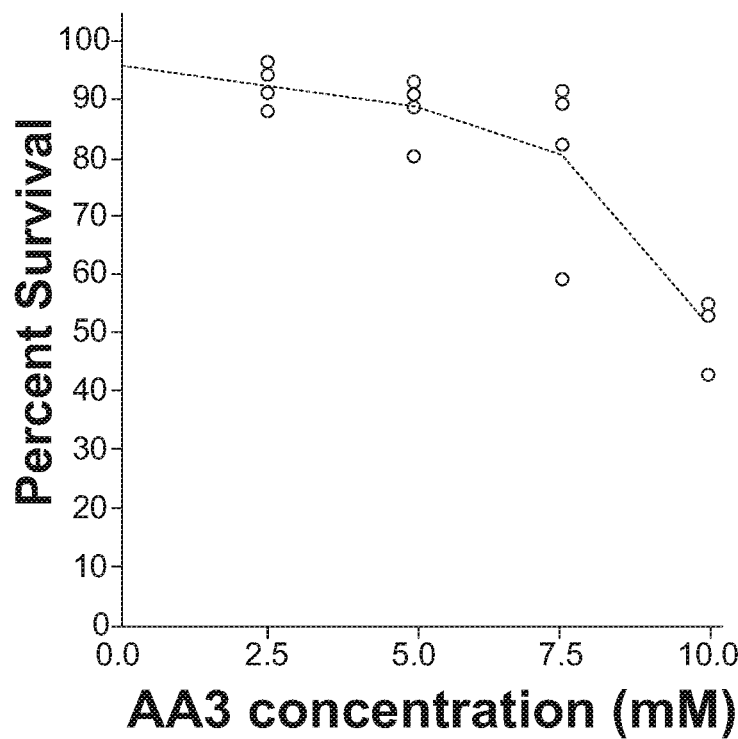
FIGS. 28A and 28B show the killing of HeLa cells by combining MMS with MX or AA3. (A) HeLa cells were treated with 50 μM MMS and different concentrations of AA3 and cell killing was determined by Trypan Blue exclusion assay. Each circle represents the result from one independent culture and the broken line connects median values at each AA3 concentration. (B) HeLa cells were treated with only AA3 (10 mM) or MMS (50 M); or treated together with MMS and MX (10 mM) or AA3 (10 mM), and cell killing was quantified. The results are from six independent cultures and the mean and standard deviation is shown in each case.
Figure 28B:
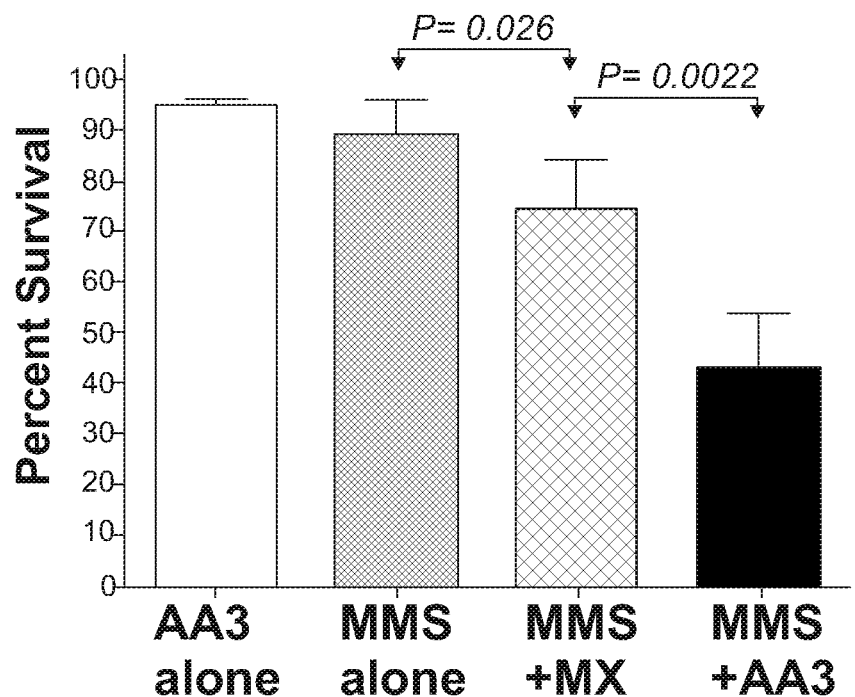

Inhibition of base-excision repair has been proposed as a strategy for anti-cancer chemotherapy [38, 39]. In particular, it has been shown that coupling treatment of cancers with alkylating agents such as MMS or temozolomide with BER inhibitor MX increases killing of tumor cells (24, 40). To determine whether AA3 is also able to enhance killing cells treated with an alkylating agent, we combined MMS treatment of HeLa cells with AA3 treatment. The results are shown in FIG. 28. When the cells were treated with a low concentration of MMS (50 M, FIG. 28A) or 10 mM AA3 (FIG. 28B), very little loss of viability was observed after one day. In fact, even 20 mM AA3 killed only ~10% of HeLa cells. However, when HeLa cells were treated with 50 M MMS and different concentrations of AA3, cell viability decreased with increasing concentration of AA3 dropping to about 50% survival at 10 mM AA3 (FIG. 28A). We then directly compared the ability of MX and AA3 to enhance killing by MMS at this concentration using six independent cultures for each chemical. The results showed that while MX did enhance killing by MMS, AA3 had a stronger lethal effect (FIG. 28B). The difference between the killing enhancement caused by MX and AA3 was statistically significant and suggests that AA3 would be better than MX as a component in anti-cancer combination chemotherapy regimen. It is unclear why AA3 kills MMS treated cells better than MX, despite the fact that both chemicals appear to be equally effective at inhibiting APE-1 and we are investing this phenomenon further. In summary, we have designed a small molecule, AA3, that can be used to quantify aldehydic lesions and AP sites in DNA in multi-titer plate format without the use of proteins. AA3 has much higher reactivity toward AP sites at physiological pH than ARP and this opens up the possibility that AA3 may be more effective at labeling AP sites in live cells. The use of click chemistry allows introducing a variety of fluorescent tags at AP sites and the biorthogonal nature of click chemistry should allow the fluorescent labeling reaction to be performed in permeabilized or fixed cells. AA3, like MX, is an efficient inhibitor of mammalian APE-1 and works better than the latter in killing cells treated with the alkylating agent MMS. Therefore, AA3 is more sensitive and versatile than ARP for labeling and quantifying AP sites, and is more effective than MX in combination chemotherapy against HeLa cells. Experiments are underway to determine whether AA3 is more effective in killing other types of cancer cells in combination with known anticancer agents.

3. Labeling Blood Samples

Using the same strategy as set forth above, we also use AA3 to quantify uracils in DNA present in milliliter amounts of patient blood. The procedure involves a simple bench-top centrifugation of blood to separate plasma from red blood cells. The cells in the blood band between these two layers and are called buffy coat. While the buffy coat contains tumor cells of a patient, the tumor DNA is also found in the plasma. We are able to detect increased levels of uracils in patient-derived buffy coat cells and circulating tumor DNA (ctDNA) in plasma.

Figure 29A:
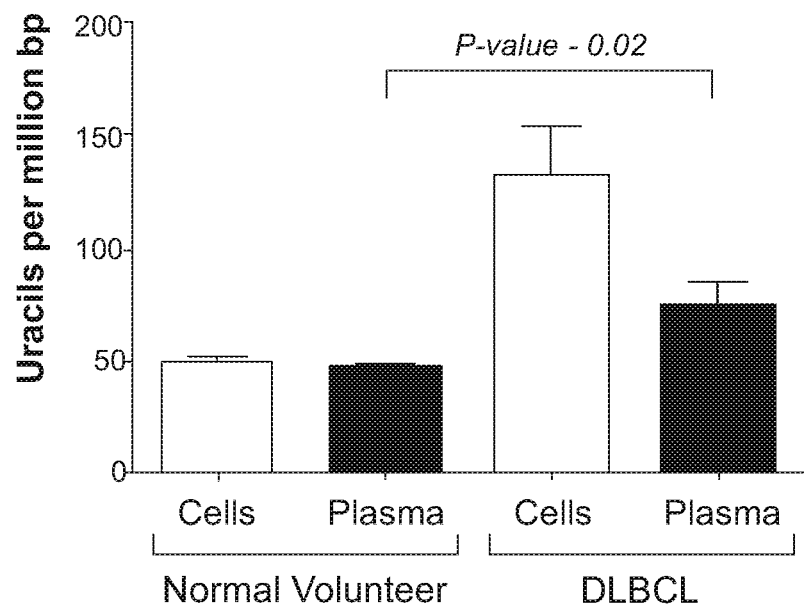
FIGS. 29A and 29B are bar charts showing that AA3 can be used to quantify genomic uracils in small amounts of patient blood.
Figure 29B:
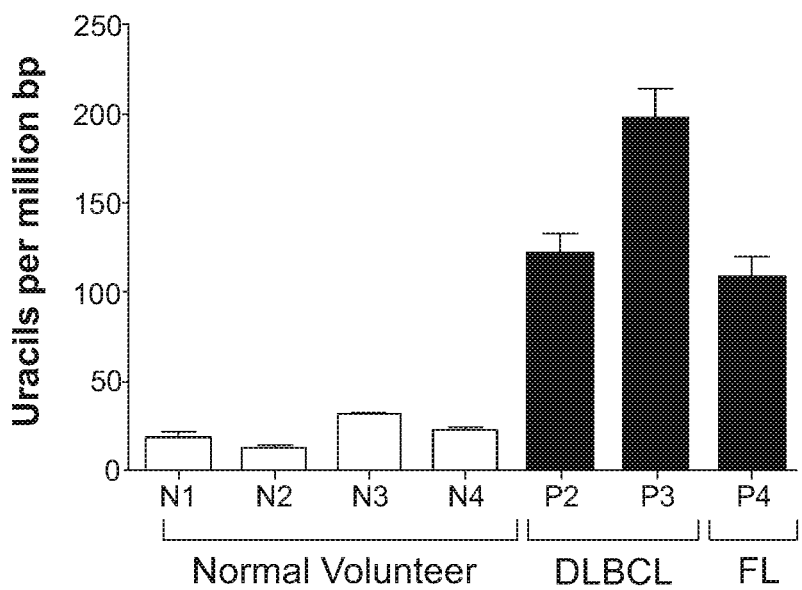

DNA was extracted from the plasma of three DLBCL and one FL patient and the uracils in these DNAs were quantified using AA3. Additionally, the uracils in buffy coat cells were also quantified for one patient. All four patients had significantly higher levels of genomic uracils than found in cells or plasma of five normal volunteers (FIG. 29). Each data point was obtained using about 1 mL of patient blood and hence it is feasible to do such a test in an outpatient basis without invasive surgery or large amounts of blood.

Imaging of B-NHL patients in remission is routinely performed in an attempt to detect asymptomatic relapse of B-NHL disease. The recommended imaging techniques include ultrasound sonography, computed tomography (CT) and positron emission tomography (PET), and the imaging is done at 6 to 12 month intervals. These are expensive surveillance techniques that require highly trained individuals for data interpretation. Thus, quantification of genomic uracils in the buffy coat or ctDNA is a simple alternative to these expensive current methods.

Therefore, AA3 may be used for detection and quantification uracils or AP sites in the tumors of patients diagnosed with B-NHL and used to decide a course of therapy (FIG. 9). If the tumor cells contain high levels of uracils and AP sites, the cells are likely to be killed by AA3. The oncologist may then recommend a course of therapy that includes AA3. If the levels of uracils and AP sites are low, other courses of treatment would be advised (FIG. 9). Following a successful course of treatment the disease would go in remission.

Such a patient in remission may also be monitored for disease relapse using AA3 (FIG. 9). Periodically, the patient would visit a clinical laboratory where a few milliliters of blood will be drawn and the buffy coat and plasma will be obtained from the blood. Following extraction of DNA from these samples, AA3 will be used to quantify uracils and AP sites in DNA. If the levels of these biomarkers remain low, the patient would be considered to be still in remission. If the levels of uracils and AP sites rise again, disease relapse would be suspected and the oncologist may order additional tests or a new course of anti-cancer therapy. Thus the same chemical, AA3, can be used for B-NHL disease surveillance and anti-cancer chemotherapy. Such a chemical is unprecedented in the literature of anti-cancer compounds.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for monitoring the presence of hematopoietic and/or lymphoid tissue cancer cells, the method comprising:
    a) obtaining a body fluid or a tissue sample from a subject suspected of having hematopoietic and/or lymphoid tissue cancer cells or a subject having been diagnosed with hematopoietic and/or lymphoid tissue cancer
    b) contacting the body fluid or the tissue sample with an alkoxyamine compound having formula IV to form a treated sample:

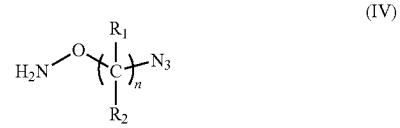

(IV)

wherein:
$R_1$, $R_2$ are each independently hydrogen (H), $C_{1-6}$ alkyl, F, Cl, or Br; and
n is 1 to 5;
    c) contacting DNA from the body fluid or the tissue sample with a probe compound that has an alkynyl functional group that reacts with and attaches to the $N_3$ (azide) moiety of formula IV to form tagged DNA, the probe compound having a probe functional group that can be used to measure the presence of and/or quantify the amount of the tagged DNA by fluorescence measurements; and
    d) detecting or measuring the amount of probe functional group to determine the presence of and/or quantify the amount of the tagged DNA, wherein the presence of and/or amount of the tagged DNA is indicative of the presence of and/or amount of hematopoietic and/or lymphoid tissue cancer cells.

2. The method of claim 1 wherein the probe functional group is a fluorophore with fluorescence measurements being performed to measure the presence of and/or quantify the amount of the tagged DNA.

3. The method of claim 1 wherein the presence or amount of uracils and/or AP sites are determined in step d) to monitor hematopoietic and/or lymphoid tissue cancer progression in the subject.

4. The method of claim 3 wherein the presence or amount of uracils and/or AP sites is used monitor progression of and/or decide a course of therapy for hematopoietic and/or lymphoid tissue cancers.

5. The method of claim 1 wherein the body fluid is blood, bone marrow, cerebral spinal fluid, peritoneal fluid, or pleural fluid.

6. The method of claim 1 wherein the body fluid is blood.

7. The method of claim 1 wherein $R_1$, $R_2$ are each hydrogen (H) and n is 1 to 2.

8. The method of claim 1 wherein n is 1.

9. The method of claim 1, wherein the probe compound having an alkynyl functional group is selected from the group consisting of 1-Ethynyl pyrene, 3-Ethynyl pyrene; BDP FL alkyne; BDP TMR alkyne; Cyanine3 alkyne; Cyanine5 alkyne; Cyanine5.5 alkyne; Cyanine7 alkyne; Cyanine7.5 alkyne; FAM alkyne, 5-isomer; FAM alkyne, 6-isomer; ROX alkyne, 5-isomer; Sulfo-Cyanine3 alkyne; Sulfo-Cyanine5 alkyne; Sulfo-Cyanine5.5 alkyne; Sulfo-Cyanine7 alkyne; and TAMRA alkyne, 5-isomer.

* * * * *